US009669009B2

(12) United States Patent
Jacob et al.

(10) Patent No.: US 9,669,009 B2
(45) Date of Patent: *Jun. 6, 2017

(54) RAPID DISPERSE DOSAGE FORM CONTAINING LEVETIRACETAM (71) Applicant: APRECIA PHARMACEUTICALS COMPANY, Langhorne, PA (US)

(72) Inventors: Jules Jacob, Yardley, PA (US); Norman Coyle, Fort Washington, PA (US); Thomas G. West, Lawrenceville, NJ (US); Donald C. Monkhouse, Radnor, PA (US); Henry L. Surprenant, Phoenixville, PA (US); Nemichand B. Jain, Princeton Junction, NJ (US)

(73) Assignee: Aprecia Pharmaceuticals Company, Langhorne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/095,785

(22) Filed: Apr. 11, 2016

(65) Prior Publication Data

US 2016/0220534 A1 Aug. 4, 2016

Related U.S. Application Data (63) Continuation of application No. 14/277,901, filed on May 15, 2014, now Pat. No. 9,339,489, which is a continuation of application No. PCT/US2014/028954, filed on Mar. 14, 2014.

(60) Provisional application No. 61/791,444, filed on Mar. 15, 2013.

(51) Int. Cl.
*A61K 31/4015* (2006.01)
*A61K 9/00* (2006.01)
*A61K 9/70* (2006.01)

(52) U.S. Cl.
CPC ........ *A61K 31/4015* (2013.01); *A61K 9/0056* (2013.01); *A61K 9/70* (2013.01); *A61K 9/7007* (2013.01)

(58) Field of Classification Search
CPC ........................ A61K 31/4015; A61K 9/0056
USPC ......................................................... 514/424
See application file for complete search history.

(56) References Cited

U.S. PATENT DOCUMENTS

| | | |
|---|---|---|
| 4,371,516 A | 2/1983 | Gregory |
| 4,642,903 A | 2/1987 | Davies |
| 4,855,326 A | 8/1989 | Fuisz |
| 4,943,639 A | 7/1990 | Gobert |
| 5,178,878 A | 1/1993 | Wehling |
| 5,283,065 A | 2/1994 | Doyon |
| 5,380,473 A | 1/1995 | Bogue |
| 5,518,730 A | 5/1996 | Fuisz |
| 5,578,322 A | 11/1996 | Shiozawa |
| 5,607,697 A | 3/1997 | Alkire |
| 5,631,023 A | 5/1997 | Kearney |
| 5,738,875 A | 4/1998 | Yarwood |
| 5,902,441 A | 5/1999 | Bredt |
| 6,416,850 B1 | 7/2002 | Bredt |
| 6,471,992 B1 | 10/2002 | Yoo |
| 6,838,035 B1 | 1/2005 | Ederer |
| 7,749,533 B2 | 7/2010 | Fu |
| 7,863,316 B2 | 1/2011 | Kshirsagar |
| 7,897,173 B2 | 3/2011 | Ziegler |
| 7,906,141 B2 | 3/2011 | Ziegler |
| 8,187,635 B2 | 5/2012 | Karavas |
| 8,802,142 B2 | 8/2014 | Deleers |
| 9,339,489 B2 | 5/2016 | Jacob |
| 2003/0133975 A1 | 7/2003 | Yoo |
| 2003/0207959 A1 | 11/2003 | Napadensky |
| 2004/0056378 A1 | 3/2004 | Bredt |
| 2004/0187714 A1 | 9/2004 | Napadensky |
| 2005/0152976 A1 | 7/2005 | Chenevier |
| 2005/0197431 A1 | 9/2005 | Bredt |
| 2007/0146734 A1 | 6/2007 | Taniuchi |
| 2007/0168815 A1 | 7/2007 | Napadensky |
| 2007/0212411 A1 | 9/2007 | Fawzy |
| 2007/0218129 A1 | 9/2007 | Besse |
| 2008/0069878 A1 | 3/2008 | Venkatesh |
| 2008/0187711 A1 | 8/2008 | Alam |
| 2008/0281019 A1 | 11/2008 | Giller |
| 2011/0318390 A1 | 12/2011 | Fuisz |
| 2012/0207929 A1 | 8/2012 | Yoo |

FOREIGN PATENT DOCUMENTS

| | | | | |
|---|---|---|---|---|
| CN | 102085194 | * | 6/2011 | ............... A61K 9/20 |
| CN | 102085194 A1 | | 6/2011 | |
| WO | 2006/102750 A1 | | 10/2006 | |
| WO | 2007/012439 A1 | | 2/2007 | |

(Continued)

OTHER PUBLICATIONS

Yu (Drug Development and Industrial Pharmacy, 2009; 35 (12): pp. 1530-1536).*
Stockis et al. ("Assessment of Levetiracetam Bioavailability From Targeted Sites in the Human Intestine . . . ", Clinical Therapeutics (2010), 32(10), 1813-1821.
Jiang et al. ("Single-dose pharmacokinetics of levetiracetam in healthy Chinese male subjects", Brit. J. Clin. Pharmacol. (2007), 63:5, 61617.
Rouits et al. ("Pharmacokinetics of levetiracetam XR 500 mg tablets", Epilepsy Res., (2009), 84, 224-231.
International Search Report for WO 2014/144512 published Sep. 18, 2014.
Keppra® (NDA N021035, UCB, Inc., approval date Nov. 30, 1999; package insert available at http://dailymed.nlm.nih.gov/dailymed/drugInfo.cfm?id=9870.
Ueda ("Levetiracetam enhances endogenous antioxidant in the hippocampus of rats: In vivo evaluation by brain microdialysis combined with ESR spectroscopy" in Brain Res. (2009), vol. 1266).

(Continued)

*Primary Examiner* — Adam C Milligan
(74) *Attorney, Agent, or Firm* — Rick Matos; Innovar, L.L.C.

(57) ABSTRACT

A high dose rapidly dispersing three-dimensionally printed dosage form comprising a high dose of levetiracetam in a porous matrix that disperses in water within a period of less than about 15 seconds is disclosed. Also disclosed are methods of preparing the dosage form and of treating a condition, disease or disorder that is therapeutically responsive to levetiracetam.

30 Claims, 1 Drawing Sheet

(56) References Cited

FOREIGN PATENT DOCUMENTS

WO    2011/136751 A1    11/2011
WO    2014/144512 A1    9/2014

OTHER PUBLICATIONS

Yu et al. ("A novel fast disintegrating tablet fabricated three-dimensional printing" in Drug Development and Indust. Pharm. (2009), 35(12), 1530-1536).
Henry et al. ("Antiepilepsy drugs: pharmacodynamics and principles of drug selection" in Epilepsy (2012), 1(6), 1-22; http://www.turner-white.com/pdf/brm_EPI_V1P6.pdf).

* cited by examiner

RAPID DISPERSE DOSAGE FORM CONTAINING LEVETIRACETAM

CROSS-REFERENCE TO EARLIER FILED APPLICATIONS

The present application is a continuation of and claims the benefit of U.S. application Ser. No. 14/277,901, filed May 15, 2014, which claims the benefit of PCT International Application No. PCT/US2014/028954 filed Mar. 14, 2014, which claims the benefit of Provisional Application No. U.S. 61/791,444 filed Mar. 15, 2013, the entire disclosures of which are hereby incorporated by reference.

FIELD OF THE INVENTION

The present invention relates to a rapidly dispersing (orodispersible) dosage form of levetiracetam. In particular, the dosage form disperses within a period of less than about fifteen seconds when placed in the mouth of subject. The invention also relates to methods of use of the dosage form for the treatment of diseases, disorders or conditions that are therapeutically responsive to levetiracetam. A process for preparing the dosage form is also provided.

BACKGROUND OF THE INVENTION

Solid oral dosage forms containing levetiracetam (LEV; (S)-2-(2-oxopyrrolidin-1-yl)butanamide; (−)-(S)-α-ethyl-2-oxo-1-pyrrolidine acetamide; described in U.S. Pat. No. 4,943,639) are known (FDA Electronic Orange Book). Solid tablets are currently available under the trademark KEPPRA® (NDA N021035, UCB, Inc., approval date Nov. 30, 1999; package insert available at http://dailymed.nlm.nih.gov/dailymed/drugInfo.cfm?id=9870). These tablets are known to contain 250, 500, 750 or 1000 mg of levetiracetam and the following excipients (inactive ingredients): colloidal silicon dioxide, croscarmellose sodium, magnesium stearate, polyethylene glycol 3350, polyethylene glycol 6000, polyvinyl alcohol, talc, titanium dioxide, and additional agents listed below: 250 mg tablets contain FD&C Blue #2/indigo carmine aluminum lake; 500 mg tablets contain iron oxide yellow; 750 mg tablets contain FD&C yellow #6/sunset yellow FCF aluminum lake, iron oxide red. KEPPRA® oral solution dosage form is also available.

Levetiracetam is very soluble in water (104.0 g/100 mL). It is freely soluble in chloroform (65.3 g/100 mL) and in methanol (53.6 g/100 mL), soluble in ethanol (16.5 g/100 mL), sparingly soluble in acetonitrile (5.7 g/100 mL) and practically insoluble in n-hexane.

LEV has been found to be chemically stable in a wide range of pharmaceutical formulations. Ingredients included in commercially available tablets of LEV include corn starch, croscarmellose sodium, povidone, colloidal silicon dioxide, talc, magnesium stearate, polyethylene glycol, titanium dioxide, iron oxide and polyvinyl alcohol, among others. However, under accelerated (60° C.) conditions of stress (acidic, alkaline, aqueous, oxidative, thermal or photo), it has been demonstrated that LEV undergoes substantial degradation (Shah, *Der Pharmacia Sinica* (2012), 3(5), 576-589). Shah reports that the rate constant for oxidative degradation is smaller than for acidic hydrolysis, base hydrolysis, water hydrolysis and UV photolysis. Prohotsky et al. (Am. J. Health Syst. Pharm. (2014), 71(3), 219-22) disclose the results of a study on the stability of an oral solution of levetiracetam. They conclude that the solution is stable for up to six months.

Ensom et al. (Can. J. Hosp. Pharm. (2011), 64(3), 207-211) disclose the results of a study on the stability of extemporaneously compounded solutions of levetiracetam in ORA-SWEET and ORA-PLUS. They report that all samples were unchanged over a period of at least 91 days.

LEV is indicated for treating epilepsy, as adjunctive treatment of partial onset seizures in adults and children 4 years of age and older with epilepsy, as adjunctive therapy in the treatment of myoclonic seizures in adults and adolescents 12 years of age and older with juvenile myoclonic epilepsy, and as adjunctive therapy in the treatment of primary generalized tonic-clonic seizures in adults and children 6 years of age and older with idiopathic generalized epilepsy. It has also been suggested for improving cognitive function in subjects that exhibit age-related cognitive impairment or are at risk thereof, including subjects having or at risk for Mild Cognitive Impairment (MCI), Age-related Cognitive Decline (ARCD) or Age-Associated Memory Impairment (AAMI).

LEV is dosed at high levels such as 250-1000 mg per tablet for the treatment of epilepsy and seizures. Treatment is initiated with a daily dose of 1000 mg/day, given as twice-daily dosing (500 mg BID). Additional dosing increments may be given (1000 mg/day additional every 2 weeks) to a maximum recommended daily dose of 3000 mg. Doses greater than 3000 mg/day have been used in open-label studies for periods of 6 months and longer. However, young and elderly patients typically experience difficulty in swallowing solid oral dosage forms containing such high doses, especially because of the large amount of excipients included in known dosage forms. Difficulty in swallowing leads to poor patient compliance. Attempts to resolve this problem have lead to the development of oral liquid and injectable formulations. Stability, contamination and inaccurate dosing problems, however, are still associated with such dosage forms.

Given the high doses of LEV required per tablet, it is difficult to formulate rapidly dispersible solid oral dosage forms with sufficient hardness and friability suitable for storage and handling. Attempts to resolve such problems are disclosed. U.S. Pat. No. 8,187,635 to Karavas et al. discloses tablets that contain dicalcium phosphate and disintegrate in about 30 min. WO 2007/012439 to UCB Pharma, S.A. discloses tablets that disintegrate in about 15-45 min. WO 2006/102750 to Genpharm Inc. discloses tablets that are made by granulation and fluid-bed drying and disintegrate in about 3 to 8 min. Such tablets do not meet the U.S. F.D.A. requirements of an orodispersible dosage form.

Orodispersible dosage forms disperse or disintegrate in the mouth in a minimal amount of saliva or water. Such dosage forms provide ease of swallowing, accuracy of dosing, and rapid therapeutic action. U.S. Pat. No. 7,749,533 to Fu et al. discloses a dosage form containing granules containing a drug, porous plastic substance, water penetration enhancer, binder and drug. The granules must be compressed in order to create the dosage form. U.S. Pat. No. 4,371,516 to Gregory et al. and U.S. Pat. No. 5,738,875 disclose freeze-dried dosage forms. U.S. Pat. No. 5,178,878 to Wehling et al. discloses a soft-compress orodispersible dosage form. Effervescent dosage forms and quick release coatings of insoluble microparticles are described in U.S. Pat. Nos. 5,578,322 and 5,607,697. Freeze dried foams and liquids are described in U.S. Pat. Nos. 4,642,903 and 5,631,023. Melt-spun dosage forms are described in U.S. Pat. Nos. 4,855,326, 5,380,473 and 5,518,730. U.S. 20070218129 discloses an immediate release dispersible and orodispersible solid pharmaceutical composition having the form of particles with a size lower than 710 μm upon dispersion into water, wherein the formulation is made by wet granulation; however, the disintegration times range from 53 to 60 sec.

U.S. Pat. No. 6,471,992, U.S. 2012-0207929 and U.S. 2003-0133975 disclose three-dimensionally printed rapidly dispersing dosage forms. Even so, an orodispersible three-dimensionally printed dosage form containing LEV has not been suggested. It is not possible to predict a priori whether a three-dimensionally printed dosage form containing substantial amounts of LEV can be made to disperse in a minimal amount of aqueous fluid in 15 sec or less 10 sec or less or 5 sec or less while at the same time possessing sufficient hardness to endure handling and storage.

None of the above discloses a rapidly dissolving solid oral dosage form containing levetiracetam. WO 2011/136751 to Mahmut discloses a compressed effervescent tablet made from a granulate containing LEV; however, the tablet dissolves in about five minutes or less. CN102085194A to Beijing Yiling Bioengineering Co. Ltd. discloses an orally distintegrating freeze-dried dosage form containing LEV, PEG 600, maltodextrin and hydrolyzed gelatin. Freeze-dried dosage forms, however, are physically very unstable and exhibit extremely high friability since they are not hard.

The use of glycerin in the manufacture of a three-dimensionally printed article is disclosed in U.S. 20080281019, U.S. 20080187711, U.S. 20070168815, U.S. 20040187714, U.S. 20030207959, U.S. 20070146734, U.S. 20050197431, U.S. 20040056378, U.S. Pat. Nos. 5,902,441, 6,416,850, and 6,838,035. There is no prior disclosure of the use of glycerin in the manufacture of a three-dimensionally printed rapidly dispersible dosage form.

It would be beneficial to provide a rapidly-dispersing orodispersible solid oral dosage form containing levetiracetam that exhibits low friability and sufficient hardness to withstand storage and handling while at the same time exhibiting an extremely rapid disintegration rate; however, no such suitable dosage form containing LEV has been disclosed in the art.

SUMMARY OF THE INVENTION

The present invention seeks to overcome some or all of the disadvantages inherent in the art. The present invention provides an orodispersible solid dosage form, as described herein, comprising levetiracetam as the primary or sole active ingredient, wherein the dosage form comprises a bound matrix that disperses in about 15 sec or less in a volume of about 10 ml or less of water or saliva. The matrix disperses in the mouth of a subject to which it is administered, thereby facilitating swallowing and administration. It would be a substantial improvement in the art to provide an orodispersible solid dosage form, as described herein, comprising levetiracetam as the primary or sole active ingredient, wherein the dosage form comprises a bound matrix that disperses in 20 sec or less in a volume of 5 ml or less of water or saliva. The matrix very rapidly disperses in the mouth of a subject to which it is administered, thereby facilitating swallowing and administration.

The dosage form is self-preserved and does not require the addition of a preservative, even though a preservative can be included if desired. Accordingly, some embodiments of the invention provide a preservative-free rapidly orodispersible dosage of LEV.

The inventors have discovered that levetiracetam undergoes oxidative degradation during formulation by three-dimensional printing; however, no degradation products corresponding to acid-catalyzed or based-catalyzed hydrolysis or photolytic or thermolytic degradation were observed. These results are surprising because (Shah, supra) teaches that oxidative degradation of LEV occurs at a much slower rate than hydrolysis or photolysis under accelerated conditions. The inventors have discovered that inclusion of an antioxidant in the orodispersible dosage form of the invention provides protection against oxidative degradation of LEV during manufacture and storage of the 3DP orodispersible dosage form. The inventors have succeeded in preparing a 3DP orodispersible dosage form comprising LEV, wherein the content of any individual oxidative degradant in the dosage form is less than 0.1% wt based upon the weight of LEV in the dosage form, wherein the dosage form comprises LEV, antioxidant, and water soluble binder comprising peroxide as impurity. The content of any individual oxidative degradant remains at or below 0.1% wt even after storage at 21° C. for six months at 75% RH.

Accordingly, some embodiments of the invention provide a stable rapidly orodispersible three-dimensionally printed solid porous matrix comprising LEV, antioxidant, disintegrant and binder, wherein the matrix is stable to oxidative degradation of LEV when stored at 21° C. for six months at 75% RH. The invention also provides a stable rapidly orodispersible three-dimensionally printed solid porous matrix comprising LEV, antioxidant, disintegrant and binder, wherein the matrix comprises 0.1% or less of an oxidative degradant of LEV after being stored at 21° C. for six months at 75% RH. In some embodiments, the antioxidant is selected from the group consisting of butylated hydroxyanisole (BHA), butylated hydroxytoluene, sodium sulfite, sodium bisulfite, methionine, vitamin E, or combinations thereof.

In some aspects, the invention provides a rapidly dispersible, i.e. orodispersible, dosage form and administration thereof for the treatment of diseases, conditions or disorders that are therapeutically responsive to levetiracetam. The rapidly dispersible solid dosage form comprises a three-dimensionally printed matrix comprising LEV, antioxidant and bulk material. The matrix is formed by deposition of a printing fluid to a powder, whereby the particles of the powder become bound by LEV and/or binder. The matrix is porous with a defined overall bulk density, disintegration (dispersion) time in aqueous fluid, dissolution time in aqueous fluid, and moisture content. The matrix provides a balance of improved chemical stability, sufficient hardness, low friability and extremely rapid dispersion time in a small volume of aqueous liquid.

Increasing the content of many different types of water soluble excipients in the 3DP orodispersible dosage form generally results in increased hardness and increased dispersion time. For example, increasing the content of water soluble binder and LEV results in increased hardness and dispersion time. The inventors have discovered that increasing the content of glycerin in the 3DP dosage form increases hardness but unexpectedly decreases dispersion time.

Accordingly, another aspect of the invention provides use of a printing fluid comprising glycerin and at least one pharmaceutically acceptable solvent for the manufacture of a rapidly dispersible dosage form. The invention also provides a three-dimensional printing system comprising a glycerin-containing printing fluid, and provides a method of three-dimensionally printing an orodispersible dosage form, the method comprising: a) depositing an incremental layer of drug-containing powder onto a surface; b) depositing a sufficient amount of printing fluid onto the incremental layer to bind particles in the powder, wherein the printing fluid comprises glycerin and at least one pharmaceutically acceptable solvent; and c) repeating a) and b) thereby forming a rapidly orodispersible.

Some embodiments of the invention include those wherein: a) the drug is water soluble drug; b) the powder and/or printing fluid comprises water soluble binder; c) the content of glycerin in the printing fluid ranges from >0% to 20% wt or about 0.05% to about 10% wt or about 0.05% to about 5% wt; and/or d) the content of glycerin in the dosage form ranges from about 0.05%-3%, or about 0.1%-2%, or 0.5%-1.0% wt based upon final weight of the dosage form.

Some aspects of the invention provide an orodispersible solid dosage form comprising a three-dimensionally printed porous matrix comprising bound particles of LEV and bulk material, wherein the particles are bound by LEV and/or binder. The invention also provides an orodispersible dosage form comprising a three-dimensionally printed matrix comprising bound particles of LEV, disintegrant, binder, and antioxidant, wherein the particles are bound by LEV and/or binder.

In some embodiments, LEV is present in crystalline form. All polymorphs thereof are contemplated. The crystallinity of LEV or any other material can be determined by differential scanning calorimetry (DSC) to determine the presence of amorphous material. In some embodiments, LEV is present in amorphous form in the bulk powder or in the matrix Embodiments of the invention include those wherein: a) the dosage form is not compressed; b) the matrix is not compressed; c) the hardness of the exterior surfaces of the dosage form is greater than the hardness of an interior portion (one or more interior incremental printed layers thereof) of the dosage form, i.e. the exterior of the dosage form is harder than the interior; d) the dissolution time of LEV is slower than the dispersion time of the matrix when placed in an aqueous fluid; e) the matrix disperses in about 10 seconds or less when placed in a small volume of aqueous fluid; f) at least 75%, at least about 90, or at least about 95% of the LEV dissolves in about 2 minutes or less when placed in an aqueous fluid; g) LEV is present in a form selected from the group consisting of hydrate, hemi-hydrate, crystalline, amorphous, anhydrate or a combination thereof; h) the dosage form comprises not more than 10% wt and not less 0.1% moisture as determined by loss on drying at 120° C.; i) the hardness of the matrix is substantially uniform; j) the dosage form comprises one or more other medicaments; and/or k) a combination thereof.

The invention also provides a three-dimensionally printed orodispersible dosage form comprising a three-dimensionally printed orodispersible matrix of bound particles, the matrix comprising LEV, disintegrant, one or more binders, one or more surfactants, one or more antioxidants, glycerin and optionally one or more of the following: one or more glidants (free-flow additive), one or more flavorants, one or more preservatives; wherein, the matrix comprises particles bound by binder and LEV; the matrix is porous and non-compressed; the matrix disperses in less than 15 sec in a volume of 10 ml of aqueous fluid; and the content of LEV in the matrix ranges from 50-80% wt based upon the total weight of the matrix. The matrix maintains a fixed and rigid three-dimensional structure when not placed in an aqueous fluid but disperses in a short period of time (as defined herein) when placed in a small volume of aqueous fluid (as defined herein).

Some embodiments of the invention include those wherein: a) the at least one surfactant is present in an amount ranging from about 0.05 to about 1%, about 0.1 to about 0.8%, and about 0.2 to about 0.5% wt based upon the final weight of the dosage form; b) the at least one antioxidant is present in an amount range from about 0.005 to about 5.0%, about 0.01 to about 1.0%, and about 0.08 to about 0.8% based upon the final weight of the dosage form; c) the at least one binder is present in an amount range from about 0.5 to about 20%, about 5 to about 15%, and about 7 to about 13% based upon the final weight of the dosage form; d) the at least one disintegrant is present in an amount range from about 3 to about 35%, about 10 to about 30%, and about 20 to about 26% based upon the final weight of the dosage form; and/or e) the at least one glidant is present in an amount range from about 0.1 to about 2.0%, about 0.25 to about 1.5%, and about 0.5 to about 1.0% wt, based upon the final weight of the dosage form.

The LEV particles have an average, mean or median particle size in the range of about 50 to about 400 microns, about 50 to about 300 microns, about 50 to about 250 microns, about 60 to about 250 microns, about 60 to about 100 microns, or about 75 to about 250 microns. The particle size can be expressed as VMD. In some embodiments, the particle size range is defined as: a) Dv10 is about 20-60 microns, Dv50 is about 50 to 200 microns, and Dv90 is about 100-500 microns; b) Dv10 is about 50-60 microns, Dv50 is about 150 to 200 microns, and Dv90 is about 350-510 microns; c) Dv10 is about 20-30 microns, Dv50 is about 50 to 60 microns, and Dv90 is about 100-120 microns; d) Dv10 is about 30-40 microns, Dv50 is about 70-80 microns, and Dv90 is about 160-190 microns; or e) Dv10 is about 40-50 microns, Dv50 is about 125 to 150 microns, and Dv90 is about 300-350 microns. In some embodiments, the VMD ranges from about 60 to about 240 microns, from 50-70 microns, from 80-100 microns, from 150 to 175 microns, from 200 to 250 microns.

Some embodiments of the invention include those wherein the matrix comprises about 250 to about 1000 mg, about 250 mg, about 500 mg, about 750 mg, about 1000 mg of LEV.

The matrix rapidly disperses (disintegrates) in a small amount of aqueous fluid. Some embodiments of the invention include those wherein the matrix disperses in about 30 sec or less, about 20 sec or less, about 15 sec or less, about 10 sec or less, or about 5 sec or less when placed in a small amount of aqueous fluid.

Some embodiments of the invention include those wherein: a) the hardness of the matrix ranges from about 1 to about 10 kp, about 2 to about 6 kp or about 3 to about 9 kp; b) the matrix disperses in 10 sec or less when placed in 15 ml of water or saliva; c) binder is introduced into the matrix by way of printing fluid used to form the matrix; d) binder is introduced into the matrix by way of bulk powder used to form the matrix; e) the matrix comprises about 250 mg to about 1000 mg of LEV; f) the matrix comprises 15 to 50 or 25 to 50 of printed incremental layers; g) the thickness (height) of an incremental layer ranges from 0.008 to 0.012 inches; and/or h) the matrix is porous and non-compressed.

The invention also provides a method of preparing a three-dimensionally printed orodispersible dosage form comprising LEV. The method comprises: a) providing an incremental layer of bulk powder comprising LEV, disintegrant, binder, antioxidant, optional flavorant, optional sweetener, and optional glidant; b) according to a predetermined saturation level, applying a printing fluid to the layer of bulk powder to form an incremental printed layer, wherein the fluid comprises water, alcohol, binder, antioxidant, glycerin, surfactant (emulsifier), optional sweetener, optional preservative; and c) repeating a) and b) at least two times, thereby forming the three-dimensionally printed orodispersible dosage form comprising at least three stacked incremental printed layers. The antioxidant can be included in the binding fluid, the powder or both.

Some embodiments of the invention include those wherein: a) the process further comprises forming an indicum or indicia on the surface of the dosage form in embossed (raised) or debossed (recessed) form during the 3DP process; b) the process further comprises removing water and alcohol from the dosage form to reduce its moisture content to within a range as described herein; c) the process further comprises separating the dosage form from bulk powder that has not been printed upon; d) a higher printing fluid saturation level is used for the upper and lower incremental layers of the dosage form than for the rest of the dosage form to provide, in the finished dosage form, increased hardness for the upper and lower incremental surfaces and reduced hardness for incremental layers there between; e) a higher printing fluid saturation level is used for the upper and lower incremental layers and for the periphery of the intermediate incremental layers of the dosage form than for the rest of the dosage form to provide, in the finished dosage form, increased hardness for its upper and lower incremental surfaces and for the periphery of its intermediate incremental layers and to provide reduced hardness for incremental layers there between; f) the process further comprises heating the dosage form to remove and reduce the amount of printing fluid therein; and/or g) the process further comprises preparing the bulk powder by mixing the ingredients thereof to form a mixture that is then sieved.

Some embodiments of the invention include those wherein the printing fluid saturation level used to prepare the incremental printed layers ranges from 40% to 120%.

A method of treating a disease or disorder that is therapeutically responsive to LEV is provided. The method comprises daily administration of one, two or three dosage forms of the invention to a subject in need thereof over a treatment period lasting days, weeks or months thereby reducing or eliminating one or more symptoms of the disease or disorder. In some embodiments, a 3DP dosage form described herein comprising a dose of about 250 to about 1000 mg is administered twice daily for a treatment period. The invention also provides a method of treating epilepsy, or other disease, disorder or condition that is therapeutically responsive to LEV, comprising: orally administering to a subject in need thereof a LEV-containing three-dimensionally printed orodispersible dosage form as described herein.

A method of preparing an orodispersible dosage form is also provided. The method comprises forming a non-compressed porous matrix as described herein by forming incremental layers of powders and depositing printing fluid on each incremental layer to bind disintegrant, binder, surfactant, antioxidant, glidant and LEV into a rapidly orodispersible non-compressed porous matrix.

The invention includes all combinations of the aspects, embodiments and sub-embodiments of the invention disclosed herein.

BRIEF DESCRIPTION OF THE DRAWINGS

The following figures form part of the present description and describe exemplary embodiments of the claimed invention. The skilled artisan will, in light of these figures and the description herein, be able to practice the invention without undue experimentation.

DETAILED DESCRIPTION OF THE INVENTION

As used herein and unless otherwise specified, the term levetiracetam (LEV) refers to the drug in underivatized form ((S)-2-(2-oxopyrrolidin-1-yl)butanamide; (−)-(S)-α-ethyl-2-oxo-1-pyrrolidine acetamide; described in U.S. Pat. No. 4,943,639) or derivatized form. Levetiracetam is available from TEVA (Jerusalem, Israel) and Hetero Labs (Hyderabad, India), Esteve (Tarragona, Spain), Aurobindo (Hyderabad, India), Matrix Labs (Karachi, Pakistan), Srini (Hyderabad, India). LEV can be present in crystalline or amorphous form. All polymorphs of crystalline LEV and mixtures thereof can be used.

The dosage form of the invention undergoes immediate and very rapid disintegration/dispersion of its solid matrix, and LEV and excipients in the matrix undergo a rapid dispersion even when placed in a small volume of aqueous fluid, such as water, saliva, juice, milk, beverage, body fluid, soda or a combination thereof. Dispersion (used interchangeably with disintegration) typically, but not necessarily, overlaps with the dissolution. The matrix comprises a three-dimensional shape that is dispersed within the desired time period upon contact of the composition with at least a small volume of aqueous fluid.

The present invention provides a pharmaceutical composition suitable for administration to a subject, the composition comprising LEV contained in a rapidly dispersing, non-compressed solid matrix, the matrix having a fixed three-dimensional shape and comprising a bulk material and a binder, the bulk material comprising a pharmaceutically acceptable compound in particulate form and the binder comprising a pharmaceutically acceptable, substantially water-soluble substance having the capacity to adhere to and bind together the particles of the bulk material, to maintain the three-dimensional shape of the matrix, when not placed in an aqueous liquid, and to permit the composition to exhibit hardness and friability characteristics adequate for storage and handling. In some embodiments, the matrix comprises LEV, binder, disintegrant, glycerin, and surfactant.

Three-dimensionally printed (3DP) dosage forms comprising the matrix were prepared according to Example 1. The resulting 3DP dosage forms were evaluated (Example 3) for hardness, dispersion time and friability to determine which of the drug-containing particles provided suitable 3DP orodispersible dosage forms with very rapid dispersion times, adequate hardness and minimal friability.

It has been determined that inclusion of a surfactant in the printing fluid, bulk powder and drug-containing particles aids in ensuring rapid dispersion of the 3DP dosage form when placed in a minimal amount of water. The surfactant serves to enhance wetting of the particles. The surfactant need only be present in an amount sufficient to enhance dispersion as compared to another 3DP dosage form excluding the surfactant. If the surfactant is present in too high of an amount, however, it will negatively impact mouth feel, performance and/or physical properties of the dosage form. The surfactant can be included in the bulk powder and/or printing fluid. In some embodiments, the amount of surfactant present in the printing fluid ranges from about 0.1 to about 4%, about 1 to about 3% or about 1.5 to about 2.5% wt. based upon the weight to the printing fluid.

The rapidly dispersible dosage form can disperse (disintegrate) in about 20 seconds or less, in about 15 seconds or less, in about 10 seconds or less, in about 5 sec or less, in about 4 sec or less, or in about 3.5 sec or less when placed in a small volume of aqueous fluid, such as a saliva, gastric fluid and/or a sip of water. In some embodiments, the dispersion (disintegration) time is measured in a small volume of 20 ml or less, 15 ml or less, 10 ml or less, 5 ml or less, 3 ml or less and at least 1 ml of an aqueous fluid. In some embodiments, the disintegration time is determined according to USP <701>.

The small volume of aqueous fluid can be a sip such as a volume less than 50 ml, less than 40 ml, less than 30 ml, less than 20 ml, less than 10 ml, less than 5 ml, less than 2.5 ml, or less than 1 ml. The small volume can be at least 0.1 ml, at least 0.25 ml, at least 0.5 ml, at least 0.75 ml, at least 1 ml, at least 1.5 ml or at least 2 ml. All possible combinations of these volumes are contemplated. Suitable ranges for the small volume include 0.1 to 50 ml, 0.1 to 40 ml, 0.1 to 30 ml, 0.1 to 20 ml, 0.1 to 10 ml, 0.2 to 10 ml, 0.3 to 10 ml, 0.5 to 10 ml, 1 to 10 ml, 1 to 7.5 ml, 1 to 5 ml, 0.5 to 3 ml, or other such ranges. Preferably a sip is about 2 to about 30 ml, about 10 to about 15 ml (1 tablespoon) or about 13 ml of water (fluid).

In some embodiments, the dosage form comprises not more than 10% wt., not more than 7.5% wt., not more than 5% wt., not more than 4% wt., not more than 3% wt., not more than 2.5% wt., not more than 2% wt. or not more than 1.5% wt. moisture as determined by loss on drying (LOD) at 120° C. In some embodiments, the dosage form comprises at least 0.1% wt., at least 0.2% wt., at least 0.5% wt., at least 0.75% wt., at least 1% wt., at least 1.5% wt., at least 2% wt., at least 2.5% wt., at least 3% wt., at least 4% wt., or at least 5% wt. moisture as determined by loss on drying at 120° C. In some embodiments, the dosage form comprises 0.1 to 10% wt, 0.2 to 7.5% wt, 0.5 to 5% wt, 0.5 to 4% wt or 1 to 3% wt moisture. All combinations of these various limits are within the scope of the invention.

The dosage form is a rapidly dispersing dosage form having superior overall hardness and friability characteristics. The hardness of the matrix can be the same (uniform) throughout the matrix, or it can vary. In some embodiments, the hardness of the exterior surfaces of the dosage form (or matrix) is greater than the hardness of an interior portion of the dosage form (or matrix), i.e. the exterior of the dosage form is harder than the interior. The exterior hardness can be at least 1.05-fold, at least 1.1-fold, at least 1.2-fold, at least 1.3-fold, at least 1.4-fold, at least 1.5-fold, at least 1.75-fold, at least 2-fold, at least 2.5-fold, at least 3 fold, at least 5-fold, at least 7-fold, or at least 10-fold higher than the interior hardness. In some embodiments, the upper and lower exterior surfaces have a greater hardness than the interior portion (one or more interior layers) of the dosage form. Methods of achieving uniform hardness and varying hardness of the matrix are discussed herein. In some embodiments, the dosage form has a shelf life of at least six months or at least one year.

In some embodiments, the overall hardness (as determined by a tablet breaking force assay according to USP <127>) of the matrix ranges from 1 kp to about 20 kp, from about 1 kp to about 10 kp, from about 1 kp to about 7 kp, from about 3 to about 9 kp, about 1 to about 3 kp, about 4.5 to about 6 kp, about 2.5 to about 6.5 kp, about 3 to about 6 kp, or from about 1 kp to about 5 kp. In some embodiments, the overall hardness is at least 1 kp, at least 2 kp, or at least 3 kp. In some embodiments, the overall hardness is no more than 10 kp, no more than 8 kp or no more than 6 kp.

The term friability refers to the tendency of the matrix to lose material from its outer edges and surfaces upon mechanical insult. Friability is reduced by increasing the hardness. In some embodiments, the dosage form possesses a friability of less than about 25%, preferably less than about 10% as determined according to USP <1216> and as further described below.

In some embodiments, the porosity of the matrix ranges from about 10% to about 90% or from about 30% to about 70% of the dosage form volume.

In some embodiments, the bulk density of the matrix (as determined by measurement and/or calculation) ranges from 150 (mg/mL) to about 1300 (mg/mL) or from about 400 (mg/mL) to about 1000 (mg/mL).

Dissolution time of the LEV is slower than dispersion time of the matrix of the dosage form when placed in an aqueous fluid. Some embodiments of the invention include those wherein not less than 75% wt. (or wherein at least 75% wt.) of LEV present in the dosage form dissolves in 20 min or less, 10 min or less, 5 min or less, 4 min or less, 3 min or less, 2 min or less or 1 min or less when placed in an aqueous environment. Other embodiments of the invention include those wherein not less than 95% wt. (or wherein at least 95% wt.) of LEV present in the dosage form dissolves in 20 min or less, 10 min or less, 5 min or less, 4 min or less, 3 min or less, 2 min or less or 1 min or less when placed in an aqueous environment or in water. In some embodiments, the dissolution times above may be achieved in aqueous environments characterized by a pH of 1.2 or 4.5 or 6.8, and tested within a USP paddle apparatus at 50 RPM or 75 RPM or 100 RPM and a volume of 900 mL or 950 mL or 1000 mL.

The rapidly dispersible dosage form of the invention is made by a three-dimensional printing (3DP) process. Suitable equipment assemblies for three-dimensional printing of articles are commercially available or are already in use: Massachusetts Institute of Technology Three-Dimensional Printing Laboratory (Cambridge, Mass.), Z Corporation's 3DP and HD3DP™ systems (Burlington, Mass.), The Ex One Company, L.L.C. (Irwin, Pa.), Soligen (Northridge, Calif.), Specific Surface Corporation (Franklin, Mass.), TDK Corporation (Chiba-ken, Japan), Therics L.L.C. (Akron, Ohio, now a part of Integra Lifesciences), Phoenix Analysis & Design Technologies (Tempe, Ariz.), Stratasys, Inc.'s Dimension™ system (Eden Prairie, Minn.), Objet Geometries (Billerica, Mass. or Rehovot, Israel), Xpress3D (Minneapolis, Minn.), and 3D Systems' Invision™ system (Valencia, Calif.). Other suitable 3DP systems are disclosed in U.S. No. 20080281019, No. 20080277823, No. 20080275181, No. 20080269940, No. 20080269939, No. 20080259434, No. 20080241404, No. 20080231645, No. 20080229961, No. 20080211132, No. 20080192074, No. 20080180509, No. 20080138515, No. 20080124464, No. 20080121172, No. 20080121130, No. 20080118655, No. 20080110395, No. 20080105144, No. 20080068416, No. 20080062214, No. 20080042321, No. 20070289705, No. 20070259010, No. 20070252871, No. 20070195150, No. 20070188549, No. 20070187508, No. 20070182799, No. 20070182782, No. 20060268057, No. 20060268044, No. 20060230970, No. 20060141145, No. 20060127153, No. 20060111807, No. 20060110443, No. 20060099287, No.

20060077241, No. 20060035034, No. 20060030964, No. 20050247216, No. 20050204939, No. 20050179721, No. 20050104241, No. 20050069784, No. 20050061241, No. 20050059757, No. 20040265413, No. 20040262797, No. 20040252174, No. 20040243133, No. 20040225398, No. 20040183796, No. 20040145781, No. 20040145628, No. 20040143359, No. 20040141043, No. 20040141030, No. 20040141025, No. 20040141024, No. 20040118309, No. 20040112523, No. 20040012112, No. 20040005360, No. 20040005182, No. 20040004653, No. 20040004303, No. 20040003741, No. 20040003738, No. 20030198677, No. 20030143268, No. 20020125592, No. 20020114652, No. 20020079601, No. 20020064745, No. 20020033548, No. 20020015728, No. 20010028471, and No. 20010017085; U.S. Pat. Nos. 5,490,962, 5,204,055, 5,121,329, 5,127,037, 5,252,264, 5,340,656, 5,387,380, 5,490,882, 5,518,680, 5,717,599, 5,851,465, 5,869,170, 5,879,489, 5,934,343, 5,940,674, 6,007,318, 6,146,567, 6,165,406, 6,193,923, 6,200,508, 6,213,168, 6,336,480, 6,363,606, 6,375,874, 6,508,971, 6,530,958, 6,547,994, 6,596,224, 6,772,026, 6,850,334, 6,905,645, 6,945,638, 6,989,115, 7,220,380, 7,291,002, 7,365,129, 7,435,368, 7,455,804, 7,828,022, 8,017,055; PCT International Publications No. WO 00/26026, No. WO 98/043762, No. WO 95/034468, No. WO 95/011007; and European Patent No. 1,631,440, which employs a cylindrical (radial or polar) coordinate-based system due to its construction. The entire disclosure of each of these references is hereby incorporated herein.

The 3DP process described herein requires a powder layering system that forms a layer of powder and printing system that applies a printing fluid to the layer of powder according to a predetermined pattern, thereby forming an incremental printed layer. The printing fluid serves to form bound particles of powder, i.e. particles that are adhered to one another by one or more pharmaceutical excipients and/or one or more active ingredients. Incremental printed layers are formed one on top of another to vertically build the dosage form of the invention, thereby forming a dosage form comprising plural incremental printed layers. The process of spreading powder and depositing droplets is repeated until the desired number of layers for the dosage form is complete. The layers adhere to one another due to bleeding of printing fluid from one layer to an adjacent other layer such that one or more excipients and/or one or more active ingredients adhere to both adjacent layers. Following completion of the initial three-dimensional structure, residual printing fluid is removed from or reduced in the dosage form by drying. The evaporation of solvent during the drying process leaves a matrix having a three-dimensional architecture comprising the particles of bulk material bound by solidified binder and/or other components including one or more active ingredients and/or any optional pharmaceutically acceptable excipients.

The three-dimensional printing process is normally conducted at ambient temperatures. The process can utilize a variety of printing fluids, including biologically compatible organic and aqueous solvents. The process is additive, whereby microscopic features are incorporated layer by layer, allowing a wide range of possible architectures to be constructed precisely on a sub-millimeter scale. Using three-dimensional printing to control simultaneously both the microscopic features and the macroscopic shape, the unique drug delivery systems of the present invention are obtained.

A particularly suitable printing assembly for three-dimensional printing of the instant dosage form is described in U.S. application No. 61/696,839, filed Sep. 5, 2012, the disclosure of which is hereby incorporated by reference in its entirety. The assembly includes build modules each having an incrementally height adjustable platform disposed within a cavity of the build modules, a powder layering system, a printing system, a printing fluid removal system and a dosage form handling system.

In general, at least two components are used in the three-dimensional printing process used to prepare the matrix of the rapidly dispersing dosage forms. The first component is the bulk powder material to be included in the incremental powder layers. The second component is the printing fluid (in some cases the fluid may also contain a binder) that is dispensed by a printhead onto the powder layer. In some embodiments, the bulk powder material is comprised of one or more pharmaceutically acceptable excipients, LEV, disintegrant, binder and surfactant.

At least one component of the matrix must serve as a "binding agent" that binds particles of bulk powder together in the completed three-dimensional matrix. The binding agent produces adhesion between particles of the bulk powder. It is this adhesion that enables the dosage form to maintain a fixed shaped (geometry) and maintain its characteristics of hardness and friability adequate to permit handling and storage. The strength and extent of the particle binding depends on the proportion of the binding agent either in the powder layer or dissolved in the solvent, and is a function of the amount of fluid deposited. The term adhesion means the bonding or binding of particles of the bulk material to each other or to particles of another material present, such as particles of binder or active ingredient. There are various ways in which a binding agent can be included in the matrix. The invention contemplates a combination of one or of two or more of these different ways.

In some embodiments of the method of preparation of the matrix, binding agent is present in the bulk powder, the printing fluid, or both. A binding agent in the printing fluid can be the same as or different than a binding agent in the bulk powder.

The binding agent can be a binder, LEV, another pharmaceutical excipient, or a combination thereof. In some embodiments, the binding agent is: a) at least LEV; b) at least binder; or c) binder and LEV. In some embodiments, two or more binding agents are present in the matrix. Including a "binder" as the binding agent in the printing fluid will result in a different internal microstructure of the wafers, particularly the pore size, than the internal microstructure of an otherwise same wafer excluding binder in the binding solution. Upon printing, as the solvent evaporates, binder remains as a solid residue, which occupies void space in between powder particles, e.g. particles of disintegrant or drug. The resulting structure will have higher density compared to tablets fabricated without binder in the printing fluid.

The invention provides a process for the preparation of a rapidly dispersing solid dosage form comprising a three-dimensionally printed solid porous matrix comprising a bulk powder, binder and LEV, the process comprising: (a) providing a powdered mixture of one or more disintegrants, one or more binders, one or more glidants and LEV, together with any optional pharmaceutically acceptable excipients; (b) forming an incremental layer of the powdered mixture; (c) applying to the incremental layer droplets of printing fluid according to a predetermined pattern to form a printed incremental layer; (d) repeating (b) and (c) a predetermined number of times, thereby providing a three-dimensionally printed moist matrix; and (e) removing printing fluid from the moist matrix, thereby providing three-dimensionally printed solid porous matrix having a composition, moisture content, porosity, overall bulk density, hardness, matrix dispersion time, in vitro drug dissolution time, in vitro dispersion behavior, in vivo pharmacokinetic behavior, structure, incremental layer thickness, drug particle size, disintegrant particle size, drug content, and/or friability within the ranges specified herein.

The dosage form of the present invention may be further shaped as desired to facilitate placement thereof in the buccal cavity of a subject. One such embodiment may be a wafer-like shape.

Figure 1:
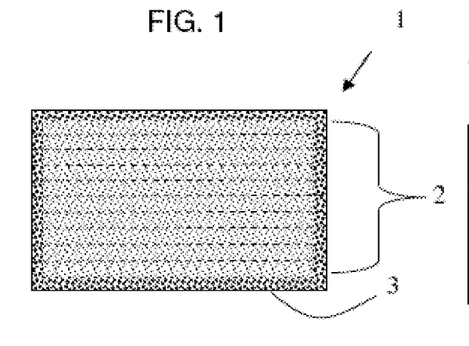
FIG. 1 depicts a sectional front elevation of an orodispersible dosage form made from a three-dimensionally printed matrix comprising sequentially-formed incremental layers of bound bulk material.

FIG. 1 depicts a sectional front elevation of an orodispersible dosage form (1) made from a three-dimensionally printed matrix comprising sequentially-formed incremental layers of bound bulk material (2-3). The exterior surfaces (3) envelope a middle portion (2). The exterior surfaces have a greater hardness than the interior portion. This dosage form is made by three-dimensionally printed plural incremental layers. The bottom incremental layer, which defines the lower surface, and the upper incremental layer, which defines the upper surface, and the circumferential surfaces (left and right of the middle portion) are harder than the interior portion. The increased hardness is achieved by using a higher saturation level, higher content of binder or as otherwise described herein. The increased hardness at the periphery of the incremental layers of the middle portion is achieved by increasing the saturation level and/or content of binder at the periphery, but not the center (non-peripheral portion) of the respective incremental layers.

Figure 2:
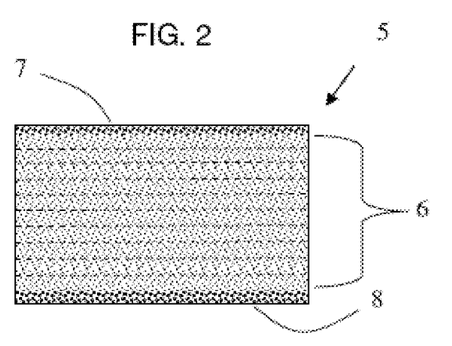
FIG. 2 depicts a sectional front elevation of an alternate embodiment of an orodispersible dosage form made from a three-dimensionally printed matrix.

FIG. 2 depicts a sectional front elevation of an alternate embodiment of an orodispersible dosage form (5) made from a three-dimensionally printed matrix. The bottom incremental layer, which defines the lower surface (8), and the upper incremental layer, which defines the upper surface (7) are harder than the interior portion (6) comprising plural incremental layers. The dosage forms (1) and (5) differ primarily in the process used to print the middle incremental layers, the layers of (6) not having a periphery with increased hardness.

Figure 3A:
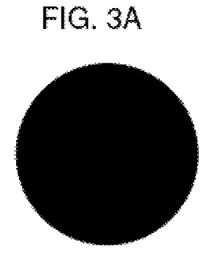
FIGS. 3A-3E depict various different printing patterns that can be used to apply printing fluid to incremental layers of powder.
Figure 3B:
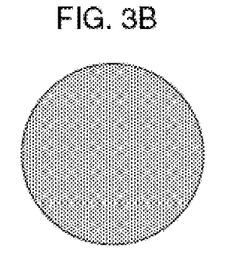

FIGS. 3A-3E depict the top plan view of three different print patterns that can be used to prepare the printed incremental layers of a 3DP orodispersible matrix of the invention. Even though each print pattern is depicted as being circular, substantially any geometry can be used, e.g. circle, oval, square, rectangle, oblong circle, etc. FIG. 3A depicts a first solid print pattern wherein substantially the same full, heavy or higher saturation level is used throughout the entire print area. FIG. 3B depicts a second solid print pattern wherein substantially the same medium, low, light or lower saturation level is used throughout the entire print area. This second solid pattern is referred to as a grayscale pattern since it has a reduced saturation level. Where solid printing is initially defined as a saturation ranging from 90 to 120%, grayscale printing is defined as saturation of less than 90%, or saturation of about 20 to <90%, or about 20 to about 85%, or about 20 to about 80%, about 20%, about 35%, about 30%, about 35%, about 40%, about 45%, about 50%, about 55%, about 60%, about 65%, about 70%, about 75%, about 80%, about 85%, or any fractional or integer increments in these ranges.

Figure 3C:
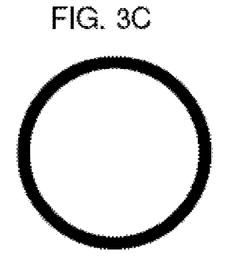
Figure 3D:
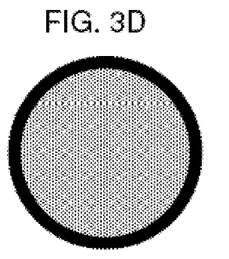

FIG. 3C depicts an annular (hollow) print pattern wherein printing fluid is applied to the periphery of the print area but not toward the center of the print area. FIG. 3D depicts a combination annular and grayscale print pattern wherein printing fluid is applied to the periphery of the print area at a higher saturation level and toward the center of the print area at a grayscale (reduced) saturation level. The radial thickness (as measured from the center of the circle) of the peripheral ring in the print patterns in FIGS. 3C and 3D can be varied as needed. The ring thickness can range from about 0.05 to 10 mm depending upon the diameter of the dosage form. It can range from about 0.1 to about 7 mm, about 0.5 to about 7 mm, about 1 to about 5 mm, or about 1.5 to about 3.5 mm.

Figure 3E:
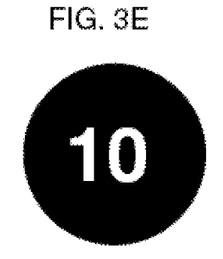

FIG. 3E depicts an indicum print pattern wherein substantially the same saturation level is used throughout the entire print area except in the indicum region(s) wherein no printing fluid is applied thereby forming a debossed indicum in the surface of the final dosage form.

In some embodiments, the dosage form comprises (consists essentially of or consists of) the following types of printed incremental layers: a) plural layers of first solid print pattern, and plural layers of combination annular and grayscale print pattern; b) plural layers of first solid print pattern, plural layers of annular print pattern, and plural layers of combination annular and grayscale print pattern; c) plural layers of first solid print pattern, plural layers of annular print pattern, plural layers of combination annular and grayscale print pattern, and plural layers of indicum print pattern; d) plural layers of first solid print pattern, plural layers of annular print pattern, plural layers of combination annular and grayscale print pattern, plural layers of first solid print pattern, and plural layers of indicum print pattern; e) plural layers of first solid print pattern, plural layers of grayscale print pattern, and plural layers of first solid print pattern; f) plural layers of grayscale print pattern; g) plural layers of combination annular and grayscale print pattern; h) plural layers of first solid print pattern; i) plural layers of first solid print pattern and plural layers of annular print pattern; or j) plural layers of first solid print pattern, plural layers of combination annular and grayscale print pattern, and plural layers of indicum print pattern.

In some embodiments, the dosage form comprises (consists essentially of or consists of) the following types of incremental layers grouped into respective sections of the dosage form: a) a first end comprising plural layers of first solid print pattern; a middle portion comprising plural layers of annular print pattern and plural layers of combination annular and grayscale print pattern; and a second end comprising plural layers of indicum print pattern; b) a first end comprising plural layers of first solid print pattern; a middle portion comprising plural layers of combination annular and grayscale print pattern; and a second end comprising plural layers of first solid print pattern and/or plural layers of indicum print pattern; c) a first end comprising plural layers of first solid print pattern; a middle portion comprising plural layers of annular print pattern, plural layers of combination annular and grayscale print pattern; and a second end comprising plural layers of first solid print pattern and/or plural layers of indicum print pattern; or d) a first end comprising plural layers of first solid print pattern; a middle portion comprising alternating groups of layers, wherein one group comprises plural layers of annular print pattern, and another group comprises plural layers of combination annular and grayscale print pattern; and a second end comprising plural layers of first solid print pattern and/or plural layers of indicum print pattern.

The physical properties of the dosage form can be controlled by varying incremental powder layer thickness, powder composition, printing fluid composition, printing fluid saturation level (print density) on a layer, and identity and amount of the excipients included within the dosage form, e.g. identity and amount of disintegrant, binder, sweetener, surfactant. These variables exhibit different levels of effect upon dosage form hardness, bulk density, disintegration time, dissolution time, bioavailability, moisture content, mouthfeel and friability. It was determined that the result effective variables include, at least, the amount of drug, amount of disintegrant, amount of binder, identity of some components, and composition of the drug-containing particles.

Three-dimensional printing can have spatial descriptors in each of three different, typically orthogonal directions. In three-dimensional printing, fluid may be deposited in drops or in fluid units resembling drops. Drops may be deposited in a succession that forms a line corresponding to the motion of the printhead. The spacing between those drops is the drop-to-drop spacing. After completion of one line, another line may be deposited adjacent to the earlier-deposited line and separated from the earlier-deposited line by a distance that is a line-to-line spacing. After completion of printing on a layer of powder, another powder layer may be deposited, with each powder layer having a layer thickness. The powder layer thickness is the third descriptor.

In some instances, the spacing of droplets may be described in terms of the resolution of the printing system, often expressed as dots per inch (dpi), which is the reciprocal of droplet spacing. For example, resolutions of 300 and 600 dpi correspond to droplet spacing's of about 84.7 microns and about 42.3 microns, respectively. The drop-to-drop spacing (within a line), or the line spacing (spacing of droplets from one line to the next), or any other spacing of droplets may be described in terms of resolution expressed in dpi. In some instances, layer-by-layer instructions for making the dosage forms may consist of a series of pixelated images characterized by a resolution in dots-per-inch in each of two orthogonal linear directions. In some instances, these pixelated images are 1-bit monochrome images, alternately referred to as binary or bi-level images in which each pixel contains one bit of information (0 or 1) that may be represented as either black or white onscreen.

In some instances, the relative amount of binding in localized regions of the dosage form is achieved by "grayscaling" (i.e., use of a grayscale print pattern) in the dosage form design. In the case of 1-bit monochrome images used for machine instructions, grayscaling is achieved by changing the number of "black" pixels relative to "white" pixels in a chosen region of a dosage form, or in a chosen layer of a dosage form, or throughout a dosage form. Any other regions that may be "solid" by using all black pixels. In some embodiments, the dosage form design includes a "solid" exterior and a "grayscaled" interior. In some embodiments, grayscaling may be achieved with equally spaced black pixels amongst white pixels to reach an overall ratio of black to white pixels in the grayscaled region. In other embodiments, grayscaling may be achieved with randomly placed black pixels amongst white pixels to achieve an overall ratio of black to white pixels in the grayscaled region. In still other embodiments, grayscaling may be achieved with a chosen pattern (e.g., parallel lines, hashed pattern, dot pattern) of black pixels amongst white pixels to achieve an overall ratio of black to white pixels in the grayscaled region.

In three-dimensional printing, a voxel or unit volume may be defined by one drop-to-drop spacing in the fast axis direction of motion, by one line-to-line spacing in the slow axis direction of motion, and by one layer thickness in the vertical direction. Some of this unit volume is occupied by powder particles, and the remainder of the unit volume is empty space that collectively has a volume that is the void volume.

The saturation level (print density) describes how much of the void space in this unit volume is occupied by liquid which is dispensed in a drop or fluid unit which is dedicated to that particular voxel. The saturation level is the ratio of the dispensed fluid volume to the volume of empty space in the voxel. In general, in three-dimensional printing, saturation levels may be chosen to be slightly less than, or somewhere approximately equal to, 1.0, also expressed as 100%. Excessively low saturation levels tend to result in poor structural integrity. Excessively high saturations levels tend to result in excessive bleeding of liquid beyond where the liquid was deposited. In the present dosage form, the saturation level during the step of applying printing fluid to a powder layer ranges from about 10% to about 110%, about 15% to about 80%, about 20% to about 50% or about 15% to about 35% in aggregate across the dosage form, or otherwise in selected regions of the dosage form.

Suitable printing devices include those having a continuous jet printhead or those having a drop-on-demand printhead. A continuous jet printhead provides a continuous jet (spray) of droplets while depositing printing fluid onto a powder layer. A drop-on-demand printhead only deposits droplets of printing fluid onto the powder layer if it receives an instruction (demand, operational command) to do so. A printhead scans (applies fluid to) the surface of powder layer from left to right at a predetermined rate, e.g. a scan rate, to form a line of droplets. A high scan rate will result in a lower saturation level, and a low scan rate with result in a higher saturation level when comparing printing fluid deposition at a constant volume per unit time. When considering the situation where binder is present in the binding solution, an increase in the print speed from 1.0 m/s to 2.0 m/s reduces the total volume of binder solution deposited in the tablets by half. As the print speed increases, the bulk density (theoretical, calculated from the weight and dimensions of the tablet) decreases. A simultaneous decrease in the dimensions and weight of the tablets is also seen. This decrease is attributed to the fact that a decrease in the total volume of binder droplets deposited onto the powder results in a decrease in the extent of binder solution spreading in the powder. Increasing the print speed also decreases the flash time and the hardness and increases the friability of the tablets. This result is obtained because the proportion of binder decreases in the tablets as the print speed increases. An increase in the print speed also increases the void volume inside the tablets, as illustrated by an increase in the percent volume of the tablets penetrated by mercury at 30 psi (% intrusion).

When using a continuous jet printhead, the printhead scans at a rate of about 0.5 to 3.0 m/sec, and most preferably at about 1.75 m/sec. When using a drop-on-demand jet printhead, the printhead scans at a rate of 0.1 to 1 m/sec, most preferably at about 0.15 to about 0.5 m/sec.

The volume of individual droplets can be varied as desired, for example, by selection of a different three-dimensional printing machine, or different printhead components on the same machine, or different parameters on the same printhead and same machine. Increasing the volume of the droplet increases the saturation level and decreasing the volume of a droplet decreases the saturation level when comparing printing fluid deposition at a constant scan rate. When using a continuous jet printhead, the size of the fluid droplets delivered by the printhead preferably ranges from about 15 µm to about 150 µm in diameter. When using a drop-on-demand printhead, the size of the fluid droplets delivered by the printhead preferably ranges from about 50 µm to about 500 µm in diameter.

The flow rate of the fluid delivered by the printhead can be varied as desired. Increasing the flow rate will increases the saturation level and decreasing the flow rate decreases the saturation level when comparing printing fluid deposition at a constant scan rate. As discussed herein, the printhead deposits droplets of printing fluid to form parallel lines thereof in the powder layer. When using a continuous jet printhead, the line spacing ranges from about 20 to about 1000 µm, about 50 to about 500 µm, or and preferably about 100 to 200 µm. When using a drop-on-demand jet printhead, the line spacing ranges from about 20 to about 300 µm, about 40 to about 100 µm, or about 55 to 75 µm.

The powder layering system and the height adjustable platform cooperate to form thin incremental layers of powder in the build modules. The total thickness (height) of the dosage form will be a function of the number and thickness of the incremental layers. The number of printed incremental layers typically ranges from 5 to 50. In some embodiments, the number of printed incremental layers ranges from 10 to 50, 15 to 45 or 20 to 40. A matrix will typically comprise (consist essentially of or consist of) 20 to 50, 20 to 40, 25 to 40, 30 to 40 or 30 to 35 printed incremental layers. The "end" section of a dosage form will typically comprise 1 to 10, 1 to 7, 2 to 7, 2 to 5, or 4 to 6 printed incremental layers. An end section with an indicum will typically comprise 2 to 10, 2 to 7, 2 to 5, or 4 to 7 printed incremental layers. The balance of the printed incremental layers will comprise the middle portion, with respect to the vertical height, of the dosage form. The middle portion will typically comprise 5 to 40, 10 to 30, 10 to 20, or 20 to 30 printed incremental layers.

Wafers (matrices, dosage forms) produced by the 3DP process described herein vary in size according to the content of LEV and of excipients required to provide dosage forms exhibiting the desired properties. If the matrix comprises a higher dose of LEV, then a larger wafer is required as compared to another 3DP dosage form having the same percentage but lower dose of LEV. If a higher percentage of LEV is used, the dosage form weight can be decreased correspondingly and vice versa. Wafer-shaped dosage forms of the invention ranged in diameter from about 13-14 mm (lowest dose) to about 20-25 mm (highest dose) and in height from about 5-6 mm (lowest dose) to about 8-10 mm (highest dose).

The incremental layers are of a predetermined height (vertical thickness), which typically varies from 0.005 to 0.015 inches, 0.008 to 0.012 inches, 0.009 to 0.011 inches, about 0.01 inches, 100-300 µm, 100-500 µm, about 200 µm, or about 250 µm. As thicker incremental layers are used, an increasing amount of printing fluid must be deposited on that layer to ensure adequate binding both within the plane of the layer and layer-to-layer. Conversely, for a thinner incremental layer a lesser amount of printing fluid must be deposited to obtain the same extent of binding. For a given amount of printing fluid deposited per layer, using a larger layer thickness will reduce (worsen) dosage form handleability and reduce (improve) dispersion time. If too thick of a layer is used for a given amount of fluid, laminar defects may form that cause the dosage form to easily fracture along the plane of the layers (delamination), or the dosage form itself may not have adequate strength to handle at all. In some embodiments, the thickness of the incremental layers ranges from 100-400 microns, 150-300 microns, or 200-250 microns. In one preferred embodiment, the layer thickness is 200 microns. In another preferred embodiment, the layer thickness is 250 microns.

The stability of LEV to oxidative degradation when included in a 3DP dosage form of the invention was determined by exposing finished dosage forms to heat. The formation of degradants was observed and monitored by HPLC/MS as detailed below. It was determined that LEV undergoes oxidative degradation to form oxo-levetiracetam whenever an antioxidant is absent and the formulation contains an oxidative excipient, e.g. povidone containing peroxide impurity or silica containing peroxide impurity. Povidone and silica, however, are important functional ingredients. Accordingly, the invention provides a stable rapidly dispersible dosage form comprising LEV, oxidative excipient, antioxidant, binder and disintegrant, wherein the matrix comprises 0.1% by wt or less of an oxidative degradant of LEV after storage for six months at 21° C. and 75% RH.

The present inventors determined that some of the excipients commonly used in 3DP dosage forms can contain oxidizing compound (oxidants), which can result from the process of manufacture or the inherent instability of the excipient(s). Some of the oxidants are believed to be peroxides. It was determined that the level of oxidant in povidone increases during storage after exposure of the excipient to an oxygen-containing atmosphere. Regardless of the source of oxidant, it is surprising that levetiracetam is so sensitive to oxidation when included in a 3DP dosage form but not when included in other dosage forms, as note in the art cited above.

Stability studies were conducted according to Example 6. The present inventors have succeeded in identifying and selecting a group of preferred antioxidants that stabilize levetiracetam against oxidation that occurs upon storage at elevated temperature and/or upon exposure to elevated temperature during the drying step of the 3DP process used to prepare the dosage form of the invention. Suitable antioxidants include sodium sulfite, sodium bisulfite, Vitamin E, methionine, BHA and BHT. Preferred antioxidants include sodium bisulfite, sodium sulfite, BHA and BHT.

One or more pharmaceutically acceptable excipients can be included in bulk powder material and/or the printing fluid. Each excipient may be independently selected upon each occurrence from a water soluble, aqueous fluid soluble, partially water soluble, partially aqueous fluid soluble, water insoluble or aqueous fluid insoluble excipient as needed to provide the required particle-to-particle binding in a printed matrix.

Most pharmaceutically acceptable excipients, both small molecules and polymers, can be employed, which allow a pharmaceutically active ingredient to be loosely encased in a porous structure (a matrix of bound particles) that is subject to rapid dispersion in the presence of an appropriate aqueous fluid, e.g., saliva. Some of these excipients, suitable for use in the three-dimensional printing process of the invention, are listed in the Handbook of Pharmaceutical Excipients (Eds. A. Wade and P. J. Weller, Second edition, American Pharmaceutical Association, The Pharmaceutical Press, London, 1994).

Suitable types of excipients include binder, disintegrant, dispersant, sweetener, glidant, flavorant, surfactant, humectant, preservative, antioxidant and diluent. Although conventional pharmaceutical excipients may be used, they may not always function in precisely the same manner as with traditional pharmaceutical processing.

One or more binders can be included in the printed matrix. The binder may be included in either the powder material or in the printing fluid dispensed through the printhead. The binder is independently selected upon each occurrence.

Adhesion of the particles to and/or by the binder occurs either when the binder is contacted by the printing fluid from the printhead or when it is present (i.e., soluble) in the printing fluid. The binder is preferably water soluble, aqueous fluid soluble, partially water soluble or partially aqueous fluid soluble. In some embodiments, the printing fluid comprises 1-20% wt, 5-15% wt or 8-12% wt of binder. In some embodiments, the bulk powder comprises >0 to 10% wt, 5 to 15% wt, 0 to 15% wt, 8-14% wt or 9-11% wt of binder. In some embodiments, the printed matrix comprises 1-20% wt, 5-14% wt or 8-12% wt of binder. In some embodiments, binder is absent from the printing fluid or absent from the bulk material.

Suitable binders include water-soluble synthetic polymer, polyvinlypyrrolidone (povidone), sorbitol, mannitiol, xylitol, lactitol, erythritol, pregelatinized starch, modified starch, hydroxypropylmethylcellulose and others. The preferred binder is polyvinylpyrrolidone, e.g. PVP K30, modified starch (e.g., starch sodium octenylsuccinate), mannitol or a combination thereof. PVP with a K value different from 30 may be used, including without limitation PVP K25 and PVP K90.

The following materials are considered binders, even though they exhibit low strength binding: spray dried lactose, fructose, sucrose, dextrose, sorbitol, mannitol, or xylitol.

One or more disintegrants can be included in the printed matrix. The disintegrant can be present in the bulk powder. The disintegrant is independently selected upon each occurrence. In some embodiments, the bulk powder comprises 5 to 30% wt, 10 to 25% wt, 15 to 25% wt, 18 to 24% wt, 18 to 23.7% wt, 1-30% wt, 10-25% wt, 20-25% wt of disintegrant.

Suitable disintegrants include microcrystalline cellulose (MCC), crospovidone (cross-linked polyvinylpyrrolidone), croscarmellose, sodium starch glycolate or a combination thereof. The preferred disintegrant is microcrystalline cellulose. Suitable grades of AVICEL® are summarized in the table below. The dosage form can comprise one or a combination of the specified grades. All such embodiments containing single grades or a combination of grades are contemplated.

| Product Grades | Nominal Particle Size, μm | Moisture, % | LooseBulk Density, g/cc |
|---|---|---|---|
| Avicel DG | 45 | NMT 5.0 | 0.25-0.40 |
| Avicel PH-101 | 50 | 3.0 to 5.0 | 0.26-0.31 |
| Avicel PH-102 | 100 | 3.0 to 5.0 | 0.28-0.33 |
| Avicel HFE*-102 | 100 | NMT 5.0 | 0.28-0.33 |
| Avicel PH-102 SCG** | 150 | 3.0 to 5.0 | 0.28-0.34 |
| Avicel PH-105 | 20 | NMT 5.0 | 0.20-0.30 |
| Avicel PH-102 SCG | 150 | 3.0 to 5.0 | 0.28-0.34 |
| Avicel PH-200 | 180 | 2.0 to 5.0 | 0.29-0.36 |
| Avicel PH-301 | 50 | 3.0 to 5.0 | 0.34-0.45 |
| Avicel PH-302 | 100 | 3.0 to 5.0 | 0.35-0.46 |
| Avicel PH-103 | 50 | NMT 3 | 0.26-0.31 |
| Avicel PH-113 | 50 | NMT 2 | 0.27-0.34 |
| Avicel PH-112 | 100 | NMT 1.5 | 0.28-0.34 |
| Avicel PH-200 LM | 180 | NMT 1.5 | 0.30-0.38 |
| Avicel CE-15 | 75 | NMT 8 | N/A |

NMT means "not more than".

The binder and disintegrant are key ingredients for controlling the hardness, friability and dispersion time of the matrix. The greater the amount of binder, the higher the hardness, the lower the friability and the slower the dispersion time. On the other hand, increasing the amount of disintegrant provides lower hardness, increased friability and a faster dispersion time. Accordingly, the matrix of the invention comprises a balanced amount of binder and disintegrant.

One or more sweeteners can be included in the printed matrix. The sweetener can be present in the bulk powder and/or in the printing fluid applied to the bulk powder. Better taste-masking is observed when at least one sweetener is present in at least the printing fluid. The sweetener is independently selected upon each occurrence. The printing fluid and the bulk powder can have at least one sweetener in common, e.g. the printing fluid and bulk powder each comprise the same sweetener and the bulk powder comprises an additional sweetener. In some embodiments, the bulk powder comprises >0 to 5% wt, or >0 to 2% wt, or >0 to 1.5% wt of sweetener. In some embodiments, the printing fluid comprises >0 to 5%, or 0.5 to 4%, or 1 to 3% wt sweetener.

Suitable sweeteners are selected from the group consisting of glycyrrhizinic acid derivative, e.g. magnasweet (monoammonium glycyrrhizinate), sucralose, aspartame, acesulfame potassium, neotame, and a combination thereof. The preferred sweetener in the printing fluid is sucralose. The sweetener is present in at least the printing fluid and can also be present in the bulk powder.

One or more flavorants can be included in the matrix. The flavorant can be present in the bulk powder and/or the printing fluid. The flavorant is independently selected upon each occurrence. The flavorant is preferably water soluble, aqueous fluid soluble, partially water soluble or partially aqueous fluid soluble. In some embodiments, the printing fluid comprises 0.01-5% wt, 0.1-1% wt or 0.2-0.5% wt of flavorant. In some embodiments, the flavorant may be provided on a powdered carrier. Suitable carriers may be chosen from starches, celluloses, and other excipients on which the flavorant could be absorbed, adsorbed, encapsulated, or otherwise loaded. In some embodiments, the bulk powder comprises 0.1 to 10% wt, or 1 to 9% wt, 2 to 8% wt of flavorant-loaded carrier. In some embodiments, the printed matrix comprises 0.1-10% wt, or 1-9% wt or 2-8% wt of flavorant-loaded carrier. In some embodiments, the flavorant is absent from the printing fluid or absent from the bulk material.

Suitable flavorants include spearmint, peppermint, mint, vanilla, orange, lemon, citrus, lime, grape, cherry, strawberry, chocolate, coffee or a combination thereof.

One or more surfactants can be included in the printing fluid and/or bulk powder. The surfactant is independently selected upon each occurrence. In some embodiments, the printing fluid comprises 0.1 to 4% wt, 1 to 3% wt or 1.5 to 2.5% wt of surfactant.

Suitable surfactants include polysorbate (PEG-ylated sorbitan (a derivative of sorbitol) esterified with fatty acid), poloxamer or a combination thereof. Suitable polysorbates include polysorbate 20 (Polyoxyethylene (20) sorbitan monolaurate), polysorbate 40 (Polyoxyethylene (20) sorbitan monopalmitate), polysorbate 60 (Polyoxyethylene (20) sorbitan monostearate), polysorbate 80 (Polyoxyethylene (20) sorbitan monooleate), sodium lauryl sulfate, poloxamer (comprising a central (poly(propylene oxide)) flanked by two chains of (poly(ethylene oxide), e.g. LUTROL), low molecular weight polyethylene glycol (e.g. PEG 400). Suitable poloxamers may include poloxamers 124, 188, 237, 338, or 407.

Even though the dosage form can be preservative-free, one or more preservatives may optionally be included in the printing fluid or powder blend. Suitable preservatives include antifungal or antimicrobial preservatives such as methylparaben and proprylparaben. In some embodiments, the printing fluid comprises 0.001 to 0.2% preservative.

One or more glidants can be included in the bulk powder. In some embodiments, the bulk powder comprises 0.1-2.0%, 0.25-1.5%, or 0.5-1.0% wt of glidant. Suitable glidants include fumed silica (colloidal silicon dioxide).

The matrix may also comprise glycerin (glycerol) introduced therein either by way of the bulk powder or the printing fluid. Glycerin can exhibit characteristics of a humectant, sweetener, preservative, lubricant, saponifier or solvent. The present inventors have discovered that glycerin unexpectedly behaves contrary to other excipients when included in a three-dimensionally printed dosage form. As noted above, increasing the amount of other excipients disclosed generally results in increased hardness with concomitantly increased disintegration time; however, increasing the amount of glycerin results in increased hardness but unexpectedly reduced disintegration time. The ability of glycerin to behave in this manner is particularly advantageous and has not been observed with any other material incorporated into a three-dimensionally printed orodispersible dosage form. Therefore, it is unexpected that one could achieve preparation of an orodispersible matrix that disperses in 10 sec or less or 5 sec or less in a small volume of water.

In some embodiments, glycerin is included in the printing fluid. Accordingly, the invention provides a printing fluid for use in three-dimensional printing wherein the printing fluid comprises glycerin, water, and at least one organic solvent. The invention also provides a three-dimensional printing method comprising: a) depositing a printing fluid comprising glycerin, water and at least one organic solvent onto at least one layer of powder; and b) reducing the content of water and solvent in the at least one layer, thereby forming a three-dimensionally printed porous matrix. The invention also provides a three-dimensional printing system comprising: a) a layer-forming system that forms layers of powder; and b) a printing fluid deposition system that deposits printing fluid onto the layers of powder, wherein the printing fluid comprises glycerin, water and at least one organic solvent.

In some embodiments, the printing fluid comprises 1-10% wt, or 2-8% wt or 3-5% wt of glycerin. In some embodiments, the matrix comprises 0.05-5% wt, 0.25-2.0% wt, 0.5-1.5% wt or 0.5-1.0% wt of glycerin.

In some embodiments, the process of the invention employs a printing fluid comprising at least one or combination of pharmaceutically acceptable solvent for at least one material in the bulk powder and/or in the printing fluid itself. The printing fluid may comprise: a) a solvent for a material in the bulk powder; b) a solvent for a material in the printing fluid; or c) a combination thereof.

Embodiments of the process of the invention include those wherein the printing fluid comprises a solvent for: a) LEV; b) a binder in the bulk powder; c) a binder in the printing fluid; d) LEV and a binder; or e) a combination thereof.

The printing fluid can comprise 55-95% wt, 60-85% wt or 65-75% wt of water or aqueous buffer.

The printing fluid can comprise 1-25% wt, 5-20% wt or 10-15% wt of at least one organic solvent. A suitable organic solvent is alcohol. Suitable alcohols include ethanol, methanol, propanol, isopropanol, or a combination thereof. In some embodiments, the alcohol is ethanol. In some embodiments, the solvent is isopropanol.

It should be understood, that compounds used in the art of pharmaceutics generally serve a variety of functions or purposes. Thus, if a compound named herein is mentioned only once or is used to define more than one term herein, its purpose or function should not be construed as being limited solely to that named purpose(s) or function(s).

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps.

The invention also provides a method of administering LEV to a subject in need thereof. The method comprises: (a) providing a rapidly dispersing, non-compressed matrix dosage form as described herein, and (b) inserting the dosage form into a moisture-containing body cavity, such as the mouth, of a subject in need thereof, the moisture being capable of dissolving the binder and dispersing the dosage form within a time period ranging from about one to about ninety seconds, thereby dispersing the dosage form in the body cavity. In some embodiments, the method further comprises the step of administering the dosage form to the subject with a sip (small volume) of fluid after the dosage form is placed in the mouth.

A study was conducted to determine whether or not the sip volume impacted the pharmacokinetic parameters of LEV following oral administration of a 3DP dosage form of the invention. Subjects were given the option to sip 30 ml or less of aqueous fluid when taking the 3DP dosage form. There was no correlation observed between sip volume and pharmacokinetic parameters observed. The sip volume ranged from 2-30 ml with an average of about 13 ml.

The invention also provides a method of treating a disease, disorder or condition that is therapeutically responsive to LEV, the method comprising: a) administering to a subject in need thereof a three-dimensionally printed orodispersible matrix as described herein or as made by the process described herein. The matrix comprises LEV, a bulk powder, disintegrant and binder, and the matrix is dispersible in a small volume of fluid. The dosage and administration regimens detailed in the package inserts for FDA approved products containing LEV, e.g. KEPPRA®, or as described herein can be followed for administering the instant dosage form.

A study was conducted according to Example 7 to determine the bioabsorption of levetiracetam when administered orally in an orodispersible 3DP dosage form of the invention. It was found that the 3DP product of the invention is equivalent to the KEPPRA® reference product in terms of the bioavailability of LEV under fasting conditions. Moreover, the 3DP product only exhibits a food effect upon Cmax and Tmax but not upon overall systemic exposure, i.e. not upon $AUC_{0-t}$ or $AUC_{inf}$. Based upon the KEPPRA® label, these results are consistent with the pharmacokinetics of KEPPRA® tablets administered in the fed state, whereby the extent of absorption is not affected but the Cmax is decreased by about 20% and the Tmax is extended by 1.5 hours Dose efficiency (AUC/dose) is a measure of how well a drug is absorbed relative to the dose of drug administered. The 3DP dosage form of the invention provides efficient bioabsorption of LEV whether administered in the fed or fasting state. The 3DP dosage form provides the following pharmacokinetic parameters when administered orally to a subject.

| Dose (mg) | $C_{max}$ (microg/ml) | $T_{max}$ (hr) | $AUC_{0-t}$ (microg-hr/ml) | $AUC_{inf}$ (microg-hr/ml) |
|---|---|---|---|---|
| 1000 (fasting) | 23-43 or 13-53 or 10-60 | 0.15-1.0 or 0.15-1.5 or 0.12-1.7 | 227-340 or 170-397 or 160-425 | 235-351 or 176-410 or 160-450 |
| 1000 (Fed) | 17-24 or 14-27 or 10-35 | 3-5 or 2-5 or 2-6 | 223-302 or 183-342 or 170-380 | 231-314 or 190-355 or 170-400 |
| 750 (fasting) | 16-31 or 9-37 or 8-40 | 0.15-1.0 or 0.15-1.5 or 0.12-1.7 | 180-270 or 135-315 or 120-350 | 186-278 or 140-324 or 120-375 |
| 750 (Fed) | 12-17 or 10-19 or 8-25 | 3-5 or 2-5 or 2-6 | 177-239 or 145-271 or 130-300 | 183-249 or 150-282 or 125-320 |
| 500 (fasting) | 9-16 or 5-20 or 4-25 | 0.15-1.0 or 0.15-1.5 or 0.12-1.7 | 119-179 or 90-209 or 80-220 | 123-185 or 93-216 or 85-240 |
| 500 (Fed) | 6-9 or 5-10 or 4-15 | 3-5 or 2-5 or 2-6 | 117-159 or 96-180 or 85-200 | 122-165 or 100-187 or 87-220 |
| 250 (fasting) | 6-11 or 3-14 or 3-18 | 0.15-1.0 or 0.15-1.5 or 0.12-1.7 | 72-108 or 54-127 or 45-150 | 75-112 or 56-131 or 47-160 |
| 250 (Fed) | 4-6 or 4-7 or 3-10 | 3-5 or 2-5 or 2-6 | 71-96 or 58-109 or 47-125 | 74-100 or 60-113 or 50-140 |

The dosage form of the invention provides a fed/fasted ratio for Cmax in the range of 0.55 to 0.74 (or about 0.6-0.7), for Tmax in the range of 5 to 21 (or about 5-13 or 5-10), for $AUC_{0-t}$ in the range of 0.89 to 0.98 and for $AUC_{inf}$ in the range of 0.89 to 0.99.

The dosage form of the invention is substantially equivalent in rate and extent of absorption to the KEPPRA® tablet, as the latter is defined by New Drug Application No. N021035 (see above), in particular when administered under fasting conditions. The dosage form provides substantially linear dose proportionality for Cmax and AUC, such that a linear fit of Cmax or AUC versus the dose administered can be characterized as having a correlation coefficient, $R^2$, of 0.95 to 1.0. The Cmax and AUC for the orodispersible dosage form are within 80-125% of the values achieved by the KEPPRA® immediate release tablet product on an equivalent dose basis.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

EXAMPLE 1

Preparation of a Three-dimensionally Printed Orodispersible Dosage Form

The following process is used to prepare a three-dimensionally printed orodispersible dosage form comprising a matrix comprising LEV. The ingredients for the printing fluid and the bulk powder are used in the amounts indicated below:

| Printing fluid | I-A | I-B | I-C | I-D |
|---|---|---|---|---|
| Water (% wt) | 68.99-70.7 | 68.47-69.12 | 66.89-67.95 | 66.5-71 |
| Glycerin (% wt) | 3.9-4 | 3.8-3.92 | 3.79-3.85 | 3.5-4 |
| Isopropanol (% wt) | 13.01-13.3 | 12.3-13.04 | 12.11-12.82 | 12-13.5 |
| Tween 20 (% wt) | 1.95-2 | 1.9-1.96 | 1.89-1.92 | 0.5-2 |
| Povidone (% wt) | 9.76-10 | 8.5-9.8 | 8.51-9.61 | 8.5-10 |
| Sucralose (% wt) | 2 | 2-5 | 4-6 | 0-3 |
| Monoammonium glycyrrhizinate (% wt) Magnasweet 100 | | | 0.2-0.6 | 0-1 |
| Spearmint Flavor HD45 | | 0.01-0.03 | 0.01-0.05 | 0-1 |
| Natural Peppermint Flavor HD29 | 0-0.38 | | | 0-1 |

| Printing fluid | I-E | I-F | I-G | I-H |
|---|---|---|---|---|
| Water (% wt) | 65-72 | 65-70 | | |
| Glycerin (% wt) | 3.5-4 | 3.4-4.2 | | |
| Isopropanol (% wt) | 12-13.5 | 11-13 | | |
| Tween 20 (% wt) | 1-2 | 1.5-2.5 | | |
| Povidone (% wt) | 8.5-10 | 8-10 | | |
| Sucralose (% wt) | >0-5 | 4-6 | | |
| Monoammonium glycyrrhizinate (% wt) Magnasweet 100 | 0-0.6 | 0.1-0.8 | | |
| Spearmint Flavor HD45 | 0-0.2 | >0-0.1 | | |
| Natural Peppermint Flavor HD29 | 0-0.5 | | | |

| Bulk powder: | II-A | II-B | II-C | II-D | II-E |
|---|---|---|---|---|---|
| LEV (% wt) | 75 | 75 | 65 | 65 | 75-90 |
| Avicel PH101 (% wt) | 17.5 | 19.8 | 21.8 | 23.8 | 5-20 |
| Mannitol (% wt) | | | 12.5 | 10.5 | |
| Povidone (PVP K29/32) (% wt) | 4.5 | 4.5 | | | 5-10 |
| Sucralose (% wt) | 2 | | | | 1-3 |
| Monoammonium glycyrrhizinate (% wt) | 0.5 | | | | 0.5 |
| Colloidal Silicon dioxide (% wt) | 0.5 | 0.7 | 0.7 | 0.7 | 0.5 |

| Bulk powder: | II-F | II-G | II-H |
|---|---|---|---|
| LEV (% wt) | 65-75 | | |
| Avicel PH101 (% wt) | 17.5-24 | | |
| Mannitol (% wt) | 10.5-12.5 | | |
| Povidone (PVP K29/32) (% wt) | 4-6 | | |
| Sucralose (% wt) | 1-3 | | |
| Monoammonium glycyrrhizinate (% wt) | 0.1-1 | | |
| Colloidal Silicon dioxide (% wt) | 0.5-0.7 | | |
| Antioxidant (% wt) | 0.1-7 | | |

An incremental layer of bulk powder of predetermined thickness is spread onto a prior layer of powder, and printing fluid is applied to the incremental layer as droplets according to a predetermined saturation level, line spacing and printing fluid flowrate to bind the particles therein. This two step process is completed until a matrix comprising the target amount of printed incremental layers.

Any three dimensional printer equipment assembly, known or mentioned herein, can be used; however, these exemplary formulations can be made with a Coriolis Instrument (Dimatix/Spectra Technology Integration, model: Coriolis RP1). The printer is operated at a droplet size of 70-90 picoliter, and resolution of 200-400 dpi or about 300 dpi by 900-1500 dpi. Various different print patterns are used in the dosage form. The specified combination of printing fluid formulation and bulk powder formulation is used. A layer thickness of 0.008 to 0.011 inches or about 0.25 to about 0.265 mm is used. A resolution of 300×1200 dpi, 300×1000 dpi, 300×900 dpi, 400×900 dpi, 400×750 dpi, 400×675 dpi is used. The printing fluids I-A through I-D are used. Many different combinations of the printing fluids and bulk powder formulations are used. Some of the resulting matrices comprise the following ingredients.

|  | III-A |
|---|---|
| LEV (% wt) | 60-70 |
| Avicel PH101 (% wt) | 20-25 |
| Mannitol (% wt) | 9.5-11 |
| Povidone (PVP K29/32) (% wt) | 1-2 |
| Sucralose (% wt) | 0.5-1.5 |
| Colloidal Silicon dioxide (% wt) | 0.5-1 |
| Moisture (% wt) | 0.3-4 |
| Glycerin (% wt) | 0.1-1 |
| Tween 20 (% wt) | 0.1-0.5 |
| Spearmint Flavor HD45 | >0-0.2 |
| Monoammonium glycyrrhizinate (% wt) | 0.05-0.15 |

The printed matrix is separated from loose unprinted powder and the printed matrix is dried by any suitable means to reduce the amount of solvent and moisture to a desired level, thereby producing the final 3DP orodispersible dosage form.

The dispersion time, surface texture (smoothness) and hardness of the dosage form are then determined.

EXAMPLE 2

Rapidly Dispersing Wafers with Varying Architecture in Different Incremental Layers Preparation of a Taste-masked Three-Dimensionally Printed Orodispersible Dosage Forms with Varying Architecture among Incremental Layers The 3DP process described above is followed; however, it can be conducted in several different ways to prepare dosage forms of different architecture varying in hardness and composition of incremental layers. The following processes provide a wafer having greater hardness in the upper and lower surfaces as compared to the hardness of the interior portion of the wafer. This tactic helps create sections within a wafer with different mechanical properties. This approach is used to design wafers in which the composition of the top and bottom layers is different from the middle layers. This design allows the wafers to have stronger top and bottom layers, thereby increasing hardness and reducing friability, and a large middle portion with lower hardness, which enables the wafer to disperse rapidly.

Method A:

In this process, the amount of binder deposited in different incremental layers or within different predefined regions within the same incremental layers is varied. The process of Example 3 is followed to prepare these wafers, except that the amount of binder, by way of the printing fluid, deposited onto the powder is varied among the incremental powder layers by using printing fluids differing in concentration of binder.

Method B:

The process of Example 3 is followed to prepare these wafers, except that the amount of printing fluid deposited onto the powder is varied among the incremental powder layers. The upper and lower incremental layers receive a higher amount of printing fluid and the incremental layers of the middle portion receive a lower amount of printing fluid.

Method C:

In this process, the printing pattern, employed for the upper and lower incremental layers of the dosage form, is a solid pattern (FIG. 3A). The printing pattern for the middle portion of incremental layers is a gray scale (FIG. 3 B). Gray scale printing can range from about 20 to about 90% or about 20 to about 80%.

Method D:

In this process, the printing pattern, employed for the upper and lower incremental layers of the dosage form, is a solid pattern (FIG. 3A). The printing pattern for the middle portion of incremental layers is an annular/hollow high saturation printing with no printing in the area surrounded by the annulus (FIG. 3C).

Method E:

In this process, the printing pattern, employed for the upper and lower incremental layers of the dosage form, is a solid pattern (FIG. 3A). The printing pattern for the middle portion of incremental layers is a combination of interior gray scale printing surrounded by an exterior high saturation printing (FIG. 3D).

EXAMPLE 3

Characterization of Dosage Forms

The following procedures were used to characterize the three-dimensionally printed solid porous orodispersible matrices.

Friability

The matrices are analyzed for their resistance to breaking using the tablet friability test (USP protocol <1216>). The test employs a VanKel friabilator (model 45-2000, Varian, USA) equipped with a drum having the dimensions of 285 mm in diameter and 39 mm deep, which is rotated at 25 rpm for 100 revolutions. A minimum number of 10 wafers are tumbled at each revolution by a curved projection that extends from the middle of the drum to the outer wall. Thus, at each turn the tablets are caused to roll or slide and fall about 130 mm onto the drum or each other. All loose powder is removed from the tablets and they are weighted collectively before and after the 100 revolutions.

Surface Texture

The matrices are inspected visually with or without the aid of a microscope. The surface texture analyzed to determine if it is rough or smooth and whether the edges of indicia on the upper surface and the edges of the perimeter of the wafer are clean and sharp or rough and jagged.

The matrices exhibited smooth surfaces with clean and sharp edges.

Hardness

The matrices are analyzed for overall hardness as determined by a tablet breaking force assay according to USP <127> ($31^{st}$ edition) using a VK 200 tablet hardness tester (Varian, US). The strength or hardness of the wafers is measured by a fracture test. A wafer is centered between the jaws of the tester and force is applied until the wafer fractures. The load at fracture is returned in kiloponds (kp). A kilopond is a metric unit of force measurement with 1 kp being equivalent to 9.807 Newtons. A minimum number of 6 wafers are tested.

The hardness of the dosage forms ranges from about 0.7 to about 5.3 kp, about 1.7 to about 5.1 kp, about 2.1 to about 5.2 kp, about 3 to about 6 kp, about 1 to about 9 kp, or about 2.5 to about 5.3 kp.

Dispersion Time

The matrices are analyzed for dispersion time in aqueous fluid as follows using a Texture Analyzer (TA HP, Texture Technologies, US) equipped with a 5 Kg load cell and a 1.0 inch diameter acrylic probe (Stable Micro Systems). The wafer is attached to the probe with double-sided adhesive tape. Under a constant 50 g force (Dor et al. in *Pharm. Dev. Technol.* (2000), 5(4), 575-577; and El-Arini et al. in *Pharm. Dev. Technol.* (2002), 7(3), 361-371), the wafer is immersed in 3 ml of water at room temperature in a flat bottom aluminum weigh boat. The dispersion time test was conducted using the following parameters. A minimum of 5 wafers was tested.

| Test mode | Compression |
|---|---|
| Pre-test speed (mm/sec) | 5 |
| Test speed (mm/sec) | 8 |
| Post-test speed (mm/sec) | 10 |
| Target mode | Force |
| Force (g) | 50 |
| Hold time (sec) | 15 |
| Trigger type | Auto (force) |
| Trigger force (g) | 5 |
| Water volume (ml) | 3 |

The dispersion time observed for the dosage forms is about 10 sec or less or about 5 sec or less.

Bulk Density

The bulk density of the matrix is determined by measuring the weight of a wafer and dividing that value by the calculated volume of the wafer. The volume of a wafer is calculated by measuring its dimensions and using the proper mathematical formula according to the shape of the wafer. For example, for a cylindrical wafer, the volume of which is calculated using the form $\pi*r^2*H$, wherein r is the radius of the water and H is its height. A wafer weighing 0.5 g, having a height of 0.6 cm and a diameter of 1.1 cm, has a volume of about 0.57 cm$^3$, and a bulk density of about 0.877 g/cm$^3$, which is equivalent to about 877 mg/ml.

Dissolution of LEV

Dissolution testing is conducted according to the Guidance for Industry (Section 3.3.2; Waiver of In Vivo Bioavailability and Bioequivalence Studies for Immediate-Release Solid Oral Dosage Forms Based on a Biopharmaceutics Classification System. August 2000. Section IIIc, p 7). The method of USP <711> was followed. Dissolution is performed using a USP Apparatus II (paddle) at 50 rpm using 900 mL of the following deaerated dissolution media: (1) 0.1N HCl; (2) 0.05 M sodium acetate, pH 4.5 buffer and (3) 0.05M KH$_2$PO$_4$, pH 6.8 buffer at 37° C.

EXAMPLE 4

In Vivo Evaluation of Three-dimensionally Printed Orodispersible Dosage Forms

This method is used to establish efficacy of the dosage form. Single dosage forms comprising LEV are administered twice daily to a subject at 12-hour intervals. Administration is done by placing the dosage form in the mouth of the subject and optionally administering a sip (5-20 ml, or 2-30 ml) of fluid to the subject. Within a short period of time, the dosage form disperses in the subject's mouth. Alternatively, the dosage form is dispersed in a minimal amount of fluid and then administered to the subject orally. The total daily dose of LEV will typically range from about 500 to about 2000 mg divided over two doses. The subject's pharmacokinetic profile is determined using known methods in the art. The subject level of therapeutic response to the dosage form is determined using known methods in the art.

EXAMPLE 5

HPLC/MS Analysis for LEV in Dosage Forms

The following procedures were used to analyze three-dimensionally printed solid porous orodispersible matrices and in support of drug-stability studies.

The following solutions were used.
Buffer: 20 mM ammonium acetate, pH 5.5
Mobile phase A (MPA): 95:5 Buffer: acetonitrile
Mobile phase B (MPB): Acetonitrile
Diluent: 95:5 water: acetonitrile
The HPLC conditions were as follows:
Column: Alltima C18 4.6×150 mm, 5 µm
Mobile phase A (MPA): 95:5 Buffer: acetonitrile
Mobile phase B (MPB): Acetonitrile
UV detection: 205 nm
Column temperature: 25° C.
Injection volume: 10 µL
Flow rate: 0.9 mL/min
Autosampler temperature: 5° C.

Samples were prepared by transferring approximately 380 mg of sample to a 50-mL volumetric flask with 30 mL of Diluent. The sample was sonicated for 10 minutes then filled to volume with Diluent. A portion was filtered through a 0.22 µm nylon filter, discarding the first 3-5 mL.

Mass spectrophotometry was conducted by directly infusing a sodium formate solution into the mass spectrometer through the lock spray at 100 µL/min using a syringe pump. The sodium formate peak at m/z 158.9646126 was used for accurate mass analysis. The accurate masses were used for elemental composition analysis using the MassLynx software.

An impurity/degradant peak had a relative retention time (RRT) of 0.64 using the client provided method. The peak had an observed, protonated, mono-isotopic mass of 185.1 Da. Accurate mass analysis and elemental composition analysis of the peak were consistent with oxo-levetiracetam.

EXAMPLE 6

Evaluation of LEV Stability in 3DP Dosage Forms

The following procedures were used to identify the preferred antioxidant(s) suitable stabilizing LEV against oxidative degradation.

A powder blend containing the following ingredients in the amounts indicated was prepared.

| Ingredient | % (w/w) |
|---|---|
| Levetiracetam, USP | 65.0 |
| Colloidal silicon dioxide, NF | 0.70 |

-continued

| Ingredient | % (w/w) |
|---|---|
| Microcrystalline cellulose, NF | 23.8 |
| Mannitol 50C, USP | 10.5 |

A printing fluid containing the following ingredients in the amounts indicated was prepared.

| Ingredient | % (w/w) | Function |
|---|---|---|
| Povidone K29/32, USP | 8.51 | Binder, viscosity modifier |
| Sucralose, NF | 5.0 | Sweetener |
| N&A Spearmint flavor HD45 | 0.03 | Flavorant |
| Glycerin, USP | 3.8 | Humectant |
| Polysorbate 20, NF | 1.9 | Surfactant |
| Isopropyl alcohol, USP | 12.3 | Solvent |
| Purified water, USP | 68.5 | Solvent |

The antioxidants evaluated are listed in the following table. Half of the amount of the IIG (Inactive Ingredient Guide) daily limit (mg) indicated in the table was used for each antioxidant since this would reach the limit when administered twice daily, which is the most common frequency of dosing immediate-release levetiracetam. For example, the amount of antioxidant would be "(IIG daily limit)/2" for a 1000 mg tablet administered twice daily. It should be understood that IIG limits are periodically changed by regulatory agencies. Accordingly, the limits specified below should be considered approximations and not as absolute limits to the amount of antioxidant that can be included in a dosage form.

| Antioxidant | IIG Daily Limit (mg) |
|---|---|
| Ascorbic acid | 28.44 |
| Butylated hydroxyanisole (BHA) | 1 |
| Butylated hydroxytoluene (BHT) | 0.36 |
| n-propyl gallate | 2 |
| L-cysteine HCl | 16.2 |
| Sodium sulfite | 0.65 |
| Sodium bisulfite | 0.65 |
| Alpha-tocopherol (Vit E) | 1.34 |
| EDTA | 100 |
| Sodium metabisulfite | 8 |
| Methionine | 5 |

The antioxidant was mixed with 6 mL of printing fluid. That mixture was then mixed with 30 g of powder blend to form a raw tablet composition, each of which was exposed to the following conditions: Condition 1—store composition at 70 C in tightly sealed glass jar; Condition 2—store composition at 50 C in loosely covered glass jar; and Condition 3—store composition at 40 C/75% RH in open glass jar.

The samples were subsequently analyzed by HPLC/MS and the identity of two key degradants was determined by comparison to standards. The key degradants were levetiracetam acid and oxo-levetiracetam. Moreover, some of the raw compositions became colored (yellowing) and others did not. The data indicate that sodium bisulfite, sodium sulfite, Vitamin E, methionine, BHA and BHT provide improved stability against oxidative degradation and against color formation. Sodium bisulfite, sodium sulfite, BHA and BHT provided the best results under the test conditions. Other antioxidants tested provided lesser degrees of protection or no protection against oxidative degradation and color formation.

EXAMPLE 7

Determination of PK Parameters for LEV in Orodispersible 3DP Dosage Forms

The following procedures were used to determine the PK parameters of the orodispersible 3DP dosage form of the invention and to compare them to those of the commercial product KEPPRA film-coated tablets.

A single center, randomized, single dose, laboratory-blinded, 3-period, 3-sequence crossover study was conducted. Thirty-two male and female subjects 18-50 yr of age and in good health were included. The subjects were orally administered single doses of a 3DP dosage form containing 1000 mg of LEV or a KEPPRA® tablet containing 1000 mg of LEV. The single dose was administered once-a-week for three weeks as follows, thereby providing a 7-day wash-out period between doses:

Group I: single dose of 3DP dosage form administered in the morning after a 10-hour overnight fast;
Group II: single dose of KEPPRA® tablet administered in the morning after a 10-hour overnight fast;
Group III: single dose of 3DP dosage form administered in the morning after a 10-hour overnight fast and 30 min after the start of a high-fat, high calorie breakfast.

The plasma concentration of LEV was determined prior to and after administration of each dose. The food effect was determined by comparing the $C_{max}$, $T_{max}$, $AUC_{0-t}$ and $AUC_{inf}$ obtained for the fasting and fed conditions. The following data provides a summary of the PK data.

| Dosage Form | $C_{max}$ (microg/ml) | $T_{max}$ (hr) | $AUC_{0-t}$ (microg-hr/ml) | $AUC_{inf}$ (microg-hr/ml) |
|---|---|---|---|---|
| KEPPRA® (fasting) | Mean: 30.48 C.V.: 19.0 | Mean: 0.58 C.V.: 69.9 | Mean: 274.9 C.V.: 18.2 | Mean: 284.3 C.V.: 18 |
| 3DP (fasting) | Mean: 33.27 C.V.: 30.1 | Mean: 0.58 C.V.: 73.7 | Mean: 283.69 C.V.: 20 | Mean: 292.9 C.V.: 19.9 |
| 3DP (Fed) | Mean: 20.48 C.V.: 16.3 | Mean: 4 C.V.: 21.6 | Mean: 262.6 C.V.: 15.1 | Mean: 272.6 C.V.: 15.2 |

It was found that the 3DP product of the invention is equivalent to the KEPPRA® reference product in terms of the bioavailability of LEV under fasting conditions. Moreover, the 3DP product only exhibits a food effect upon Cmax and Tmax but not upon overall systemic exposure, i.e. not upon $AUC_{0-t}$ or $AUC_{inf}$. These results are consistent with the pharmacokinetics of KEPPRA® tablets administered in the fed state (KEPPRA® label, NDA 021035).

As used herein, the term "about" or "approximately" are taken to mean±10%, ±5%, ±2.5% or ±1% of a specified valued. As used herein, the term "substantially" is taken to mean "to a large degree" or "at least a majority of" or "more than 50% of".

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating a disease, condition or disorder that is therapeutically responsive to levetiracetam comprising orally administering one or more times daily to a subject in need thereof a rapidly dispersible solid dosage form comprising levetiracetam in a bound porous matrix that disperses in about 15 sec or less in a volume of about 15 ml or less of water or saliva, wherein the dosage form provides a Cmax within the ranges listed below when respective doses of levetiracetam are administered to the subject in the fasting state:

| Dose (mg) | $C_{max}$ (micrograms/ml) |
|---|---|
| 1000 | 13-53 |
| 750 | 9-37 |
| 500 | 5-20 |
| 250 | 4-7 | wherein the bound porous matrix comprises 50-80% wt of levetiracetam (LEV), 3-35% wt of at least one disintegrant, and 0.5-20% wt of at least one binder wherein the matrix has a hardness of at least 2 kp.

2. The method of claim 1, wherein the dosage form provides a Tmax within the range of 0.15-1.5 hours.

3. The method of claim 1, wherein the dosage form provides an $AUC_{0-t}$, $AUC_{inf}$ or a combination of $AUC_{0-t}$ and $AUC_{inf}$ within the ranges listed below:

| Dose (mg) | $AUC_{0-t}$ (microg-hr/ml) | $AUC_{inf}$ (microg-hr/ml) |
|---|---|---|
| 1000 | 170-397 | 176-410 |
| 750 | 135-315 | 140-324 |
| 500 | 90-209 | 93-216 |
| 250 | 54-127 | 56-131. |

4. The method of claim 1, wherein the dosage form is equivalent to a KEPPRA® tablet, as defined by NDA No. N021035, in terms of $C_{max}$, $AUC_{0-t}$ and/or $AUC_{inf}$ on an equi-dose basis.

5. The method of claim 1, wherein the dosage form is administered one to three times daily, and the Cmax is determined with respect to single dose.

6. The method of claim 1, wherein the dosage form provides a fed/fasted ratio for Cmax in the range of 0.55 to 0.74 and for Tmax in the range of 5 to 21 hours.

7. The method of claim 6, wherein the dosage form provides a fed/fasted ratio, for $AUC_{0-t}$ in the range of 0.89 to 0.98 and for $AUC_{inf}$ in the range of 0.89 to 0.99.

8. The method of claim 1, wherein: a) the dosage form is not compressed; b) the matrix is not compressed; c) the exterior of the dosage form is harder than the interior; d) the dissolution time of LEV is slower than the dispersion time of the matrix when placed in an aqueous fluid; e) the matrix disperses in about 10 seconds or less when placed in a small volume of aqueous fluid; f) at least 75%, at least about 90, or at least about 95% of the LEV dissolves in about 2 minutes or less when placed in an aqueous fluid; g) LEV is present in a form selected from the group consisting of hydrate, hemi-hydrate, crystalline, amorphous, anhydrate or a combination thereof; h) the dosage form comprises not more than 10% wt and not less 0.1% moisture as determined by loss on drying at 120° C.; i) the hardness of the matrix is substantially uniform; j) the dosage form comprises one or more other medicaments; k) the matrix further comprises glycerin; l) the matrix further comprises glycerin, wherein the content of glycerin ranges from about 0.05%-3%; m) at least 95% of LEV is dissolved in 5 minutes or less in 900 ml of aqueous media at pH 1.2, 4.5 or 6.8 in a USP paddle apparatus operating at 50 RPM; or n) a combination thereof.

9. The method of claim 1, wherein the matrix further comprises one or more surfactants and one or more antioxidants, and optionally comprises one or more of the following: glycerin, one or more glidants, one or more flavorants and one or more preservatives.

10. The method of claim 9 wherein: a) the one or more surfactants is present in an amount ranging from about 0.05 to about 1% wt based upon the final weight of the dosage form; b) the one or more antioxidants is present in an amount ranging from about 0.005 to about 5.0% wt based upon the final weight of the dosage form; c) the at least one binder is present in an amount ranging from about 5 to about 15% wt based upon the final weight of the dosage form; d) the at least one disintegrant is present in an amount ranging from about 10 to about 30% wt based upon the final weight of the dosage form; e) the one or more glidants is present in an amount ranging from about 0.1 to about 2.0% wt, based upon the final weight of the dosage form; f) the matrix comprises about 250 to about 1000 mg, about 250 mg, about 500 mg, about 750 mg, about 1000 mg of LEV; or g) a combination thereof.

11. The method of claim 1, wherein: a) the hardness of the matrix ranges from about 2 to about 10 kp, about 2 to about 6 kp or about 3 to about 9 kp; b) the matrix disperses in 10 sec or less when placed in 15 ml of water or saliva; c) the matrix comprises 15 to 50 or 25 to 50 of printed incremental layers, wherein the thickness of an incremental layer ranges from 0.008 to 0.012 inches; d) the matrix is porous and non-compressed or e) a combination thereof.

12. The method of claim 1, wherein the dosage form comprises the following ingredients

| Ingredient | Amt (% wt) |
|---|---|
| LEV | 60-70 |
| Disintegrant | 20-25 |
| Binder | 10-15 |
| Sweetener | 0.5-2 |
| Glidant | 0.1-1.5 |
| Glycerin | 0.1-5 |
| Surfactant | 0.05-1.5 |
| Flavor | 0-0.5. |

13. The method of claim 1, wherein the matrix comprises 0.1% or less of an oxidative degradant of LEV after being stored at 21° C. for six months at 75% RH.

14. The method of claim 1, wherein the dosage form is preservative free.

15. A method of treating a disease, condition or disorder that is therapeutically responsive to levetiracetam comprising orally administering one or more times daily to a subject in need thereof a rapidly dispersible solid dosage form comprising levetiracetam in a bound porous matrix that disperses in about 15 sec or less in a volume of about 15 ml or less of water or saliva, wherein the dosage form provides a Cmax within the ranges listed below when respective doses of levetiracetam are administered to a subject in the fed state:

| Dose (mg) | $C_{max}$ (microg/ml) |
|---|---|
| 1000 | 14-27 |
| 750 | 10-19 |
| 500 | 5-10 |
| 250 | 4-73 | wherein the bound porous matrix comprises 50-80% wt of levetiracetam (LEV), 3-35% wt of at least one disintegrant, and 0.5-20% wt of at least one binder wherein the matrix has a hardness of at least 2 kp.

16. The method of claim 15, wherein the dosage form provides a Tmax within the range of 2-5 hours.

17. The method of claim 15, wherein the dosage form provides an $AUC_{0-t}$, $AUC_{inf}$, or a combination of $AUC_{0-t}$ and $AUC_{inf}$ within the ranges listed below:

| Dose (mg) | $AUC_{0-t}$ (microg-hr/ml) | $AUC_{inf}$ (microg-hr/ml) |
|---|---|---|
| 1000 | 183-342 | 190-355 |
| 750 | 145-271 | 150-282 |
| 500 | 96-180 | 100-187 |
| 250 | 58-109 | 60-113. |

18. The method of claim 15, wherein the dosage form is equivalent to a KEPPRA® tablet, as defined by NDA No. N021035, in terms of $C_{max}$, $AUC_{0-t}$, $AUC_{inf}$, or a combination thereof on an equi-dose basis.

19. The method of claim 15, wherein the dosage form is administered one to three times daily, and the Cmax is determined with respect to single dose.

20. The method of claim 15, wherein: a) the dosage form is not compressed; b) the matrix is not compressed; c) the exterior of the dosage form is harder than the interior; d) the dissolution time of LEV is slower than the dispersion time of the matrix when placed in an aqueous fluid; e)the matrix disperses in about 10 seconds or less when placed in an aqueous fluid; f) at least 75%, at least about 90, or at least about 95% of the LEV dissolves in about 2 minutes or less when placed in an aqueous fluid; g) LEV is present in a form selected from the group consisting of hydrate, hemi-hydrate, crystalline, amorphous, anhydrate or a combination thereof; h) the dosage form comprises not more than 10% wt and not less 0.1% moisture as determined by loss on drying at 120° C.; i) the hardness of the matrix is substantially uniform; j) the dosage form comprises one or more other medicaments; k) the matrix further comprises glycerin; l) the matrix further comprises glycerin, wherein the content of glycerin ranges from about 0.05%-3%; m) at least 95% of LEV is dissolved in 5 minutes or less in 900 ml of aqueous media at pH 1.2, 4.5 or 6.8 in a USP paddle apparatus operating at 50 RPM; or n) a combination thereof.

21. The method of claim 15, wherein the matrix further comprises one or more surfactants and one or more antioxidants, and optionally comprises one or more of the following: glycerin, one or more glidants, one or more flavorants and one or more preservatives.

22. The method of claim 21 wherein: a) the one or more surfactants is present in an amount ranging from about 0.05 to about 1% wt based upon the final weight of the dosage form; b) the one or more antioxidants is present in an amount ranging from about 0.005 to about 5.0% wt based upon the final weight of the dosage form; c) the at least one binder is present in an amount ranging from about 5 to about 15% wt based upon the final weight of the dosage form; d) the at least one disintegrant is present in an amount ranging from about 10 to about 30% wt based upon the final weight of the dosage form; e) the one or more glidants is present in an amount ranging from about 0.1 to about 2.0% wt, based upon the final weight of the dosage form; f) the matrix comprises about 250 to about 1000 mg, about 250 mg, about 500 mg, about 750 mg, about 1000 mg of LEV; or g) a combination thereof.

23. The method of claim 15, wherein: a) the hardness of the matrix ranges from about 2 to about 10 kp, about 2 to about 6 kp or about 3 to about 9 kp; b) the matrix disperses in 10 sec or less when placed in 15 ml of water or saliva; c) the matrix comprises 15 to 50 or 25 to 50 of printed incremental layers, wherein the thickness of an incremental layer ranges from 0.008 to 0.012 inches; d) the matrix is porous and non-compressed or e) a combination thereof.

24. The method of claim 15, wherein the dosage form is preservative free.

25. The method of claim 15, wherein the matrix comprises 0.1% or less of an oxidative degradant of LEV after being stored at 21° C. for six months at 75% RH.

26. The method of claim 15, wherein the dosage form comprises the following ingredients

| Ingredient | Amt (% wt) |
|---|---|
| LEV | 60-70 |
| Disintegrant | 20-25 |
| Binder | 10-15 |
| Sweetener | 0.5-2 |
| Glidant | 0.1-1.5 |
| Glycerin | 0.1-5 |
| Surfactant | 0.05-1.5 |
| Flavor | 0-0.5. |

27. The method of claim 1, wherein at least one binder is water soluble.

28. The method of claim 15, wherein at least one binder is water soluble.

29. A method of treating a disease, condition or disorder that is therapeutically responsive to levetiracetam comprising orally administering one or more times daily to a subject in need thereof a three-dimensionally printed rapidly dispersible solid bound matrix comprising 50-80% wt of levetiracetam, 3-35% wt of at least one disintegrant and 0.5-20% wt of at least one binder, wherein the matrix disperses in about 15 sec or less in a volume of about 15 ml or less of water or saliva and has a hardness of at least 2 kp.

30. The method of claim 29, wherein the three-dimensionally printed rapidly dispersible solid bound matrix is porous and non-compressed and comprises 50-80% wt of levetiracetam, 3-35% wt of at least one disintegrant, 0.5-20% wt of at least one water soluble binder, 0.005 to about 5.0% wt of one or more antioxidants, about 250 mg to about 1000 mg of levetiracetam, and not more than 10% wt and not less 0.1% moisture as determined by loss on drying at 120° C., wherein the matrix disperses in about 15 sec or less in a volume of about 15 ml or less of water or saliva and has a hardness of at least 2 kp.

* * * * *